(12) United States Patent
Malyshev et al.

(10) Patent No.: US 11,884,971 B2
(45) Date of Patent: Jan. 30, 2024

(54) COMPOSITIONS AND TECHNIQUES FOR NUCLEIC ACID PRIMER EXTENSION

(71) Applicant: Pacific Biosciences of California, Inc., Menlo Park, CA (US)

(72) Inventors: Denis Malyshev, La Jolla, CA (US); Arnold Oliphant, Morgan Hill, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 17/391,423

(22) Filed: Aug. 2, 2021

(65) Prior Publication Data

US 2022/0136045 A1 May 5, 2022

Related U.S. Application Data

(63) Continuation of application No. 16/265,942, filed on Feb. 1, 2019, now abandoned.

(60) Provisional application No. 62/626,836, filed on Feb. 6, 2018.

(51) Int. Cl.
*C12Q 1/6853* (2018.01)
*C12Q 1/6869* (2018.01)

(52) U.S. Cl.
CPC ......... *C12Q 1/6853* (2013.01); *C12Q 1/6869* (2013.01)

(58) Field of Classification Search
CPC ........ C12Q 2525/186; C12Q 2565/133; C12Q 1/6853; C12Q 1/6869
See application file for complete search history.

(56) References Cited

U.S. PATENT DOCUMENTS

| | | |
|---|---|---|
| 7,057,026 B2 | 6/2006 | Barnes et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,544,794 B1 | 6/2009 | Benner |
| 7,956,171 B2 | 6/2011 | Siddiqi |
| 8,034,923 B1 | 10/2011 | Benner et al. |
| 8,071,755 B2 | 12/2011 | Efcavitch et al. |
| 8,236,532 B2 | 8/2012 | Ronaghi et al. |
| 8,298,792 B2 | 10/2012 | Meng et al. |
| 8,753,816 B2 | 6/2014 | Rigatti et al. |
| 8,808,989 B1 | 8/2014 | Efcavitch et al. |
| 9,115,163 B2 | 8/2015 | Ju et al. |
| 9,399,798 B2 | 7/2016 | Stupi et al. |
| 9,951,385 B1 | 4/2018 | Vijayan et al. |
| 10,036,063 B2 | 7/2018 | West |
| 10,077,470 B2 | 9/2018 | Vijayan et al. |
| 10,161,003 B2 | 12/2018 | Stromberg |
| 10,246,744 B2 | 4/2019 | Vijayan et al. |
| 10,443,098 B2 | 10/2019 | Vijayan et al. |
| 2008/0108082 A1 | 5/2008 | Rank et al. |
| 2010/0279882 A1 | 11/2010 | Ronaghi et al. |
| 2017/0022553 A1 | 1/2017 | Vijayan et al. |
| 2017/0137873 A1 | 5/2017 | Nguyen et al. |
| 2017/0314064 A1* | 11/2017 | Iyidogan .............. C12Q 1/6809 |
| 2018/0044715 A1 | 2/2018 | Iyidogan et al. |
| 2018/0044727 A1 | 2/2018 | Vijayan et al. |
| 2018/0187245 A1 | 7/2018 | Dambacher et al. |
| 2018/0208983 A1 | 7/2018 | Dambacher et al. |
| 2019/0367974 A1 | 12/2019 | Fleischer et al. |
| 2020/0002762 A1 | 1/2020 | Vijayan et al. |
| 2020/0263246 A1 | 8/2020 | Shen |

FOREIGN PATENT DOCUMENTS

| | | |
|---|---|---|
| WO | WO 1991/06678 A1 | 5/1991 |
| WO | WO 2004/018497 A2 | 3/2004 |
| WO | WO 2007/123744 A2 | 11/2007 |
| WO | WO 2009/134469 A1 | 11/2009 |
| WO | WO 2009/155181 A1 | 12/2009 |
| WO | WO 2013/022961 A1 | 2/2014 |
| WO | WO 2017/184996 A1 | 10/2017 |

OTHER PUBLICATIONS

PCT, International Search Report and Written Opinion for PCT/US2019/016432, dated Feb. 1, 2019.
Chen, Z. et al., "Highly accurate fluorogenic DNA sequencing with information theory-based error correction," Nature Biotech. 35 (12), pp. 1170-1178 (Dec. 2017, e-published Nov. 6, 2017).

* cited by examiner

*Primary Examiner* — Young J Kim
(74) *Attorney, Agent, or Firm* — Orrick, Herrington & Sutcliffe, LLP

(57) ABSTRACT

A method of characterizing a nucleic acid that includes steps of (a) contacting a primer-template nucleic acid hybrid with a polymerase and a mixture of nucleotides to produce an extended primer hybrid and to form a stabilized ternary complex including the extended primer hybrid, the polymerase and a nucleotide cognate of the next base in the template, wherein the mixture contains nucleotide cognates of four different base types, wherein the nucleotide cognate of the first base type has a reversible terminator, and wherein nucleotide cognates of the second, third and fourth base types are extendable; (b) detecting the stabilized ternary complex to distinguish the next base from other base types in the template; and (c) determining the presence of a base multiplet in the template nucleic acid, the base multiplet including the first base type followed by the next base.

19 Claims, 2 Drawing Sheets
Specification includes a Sequence Listing.

COMPOSITIONS AND TECHNIQUES FOR NUCLEIC ACID PRIMER EXTENSION

CROSS-REFERENCES TO RELATED APPLICATIONS

This application is a continuation of U.S. patent application Ser. No. 16/265,942, filed Feb. 1, 2019, which claims the benefit of U.S. Provisional Application No. 62/626,836, filed Feb. 6, 2018, which are incorporated herein by reference in their entireties and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 053195-505C01US_SequenceListing_ST25.txt, created Jul. 29, 2021, 4,096 bytes, machine format IBM-PC, MS Windows operating system, is hereby incorporated by reference.

BACKGROUND

The present disclosure relates generally to molecular analysis and diagnostics and has specific applicability to nucleic acid sequencing.

The time required to sequence a human genome has dropped precipitously in the last decade. The procedure, which used to take several years and millions of dollars to perform, can now be completed in mere hours, for a few thousand dollars. Although the rate of improvement has been impressive, the currently available commercial methods are still unsatisfactory for many clinical applications.

Sequencing holds the promise, in the minds of many clinicians, to provide important information to develop a reliable diagnosis as to whether a patient has a deadly disease and to provide guidance when choosing expensive or life altering treatment options. For example, sequencing can play a key role in confirming a preliminary cancer diagnosis and helping the patient decide on treatment options. Even a few days of delay in receiving such confirmation can cause a significant adverse toll on the emotional and psychological state of the patient.

In some situations, clinical outcome is strongly dependent on a rapid diagnosis. For example, sequencing has been used in neonatal intensive care units to identify mystery diseases in newborn infants and lead doctors to otherwise unrecognized treatment options that saved lives. Nevertheless, too many newborns die every year for lack of a timely diagnosis.

Thus, there exist needs for improvements to the accuracy, speed and cost of nucleic acid sequencing. The present invention satisfies these needs and provides related advantages as well.

BRIEF SUMMARY

The present disclosure provides a method of characterizing a nucleic acid. The method can include the steps of (a) contacting a primer-template nucleic acid hybrid with a polymerase and a mixture of nucleotides under conditions to produce an extended primer hybrid, wherein the mixture includes nucleotide cognates of first, second, third and fourth different base types, wherein the nucleotide cognate of the first base type has a reversible terminator, and wherein at least one of the nucleotide cognates of the second, third or fourth base types is extendable; (b) contacting the extended primer hybrid with a nucleotide cognate for at least one of the different base types and a polymerase to form a stabilized ternary complex that includes the extended primer hybrid, the polymerase and a nucleotide cognate of the next base in the template; (c) detecting the stabilized ternary complex to distinguish the next base from other base types in the template; and (d) determining the presence of a base multiplet in the template nucleic acid including the first base type followed by the next base. Optionally, the method further includes steps of (e) repeating steps (a) through (c) using the extended primer hybrid as the primer-template nucleic acid hybrid and (f) determining the presence of a series of at least two base multiplets in the template nucleic acid. In some embodiments, the nucleotide cognate of the first base type has a reversible terminator and the nucleotide cognates of the second, third and fourth base types are extendable. Alternatively, the nucleotide cognates of the first and second base types have a reversible terminator and the nucleotide cognates of the third and fourth base types are extendable.

In a further embodiment a method of characterizing a nucleic acid can include the steps of (a) contacting a primer-template nucleic acid hybrid with a polymerase and a mixture of nucleotides under conditions to produce an extended primer hybrid, wherein the mixture includes nucleotide cognates of first, second, third and fourth different base types, wherein the nucleotide cognate of the first base type has a reversible terminator, and wherein nucleotide cognates of the second, third and fourth base types are extendable; (b) contacting the extended primer hybrid with a nucleotide cognate for at least one of the different base types and a polymerase to form a stabilized ternary complex that includes the extended primer hybrid, the polymerase and a nucleotide cognate of the next base in the template; (c) detecting the stabilized ternary complex to distinguish the next base from other base types in the template; (d) determining the presence of a base multiplet in the template nucleic acid including the first base type followed by the next base; (e) repeating steps (a) through (c) using the extended primer hybrid as the primer-template nucleic acid hybrid; (f) determining the presence of a series of at least two base multiplets in the template nucleic acid; and (g) repeating steps (a) through (f), wherein the nucleotide cognate of the second base type includes a reversible terminator, and wherein nucleotide cognates of the first, third and fourth base types in the mixture are extendible, and wherein the base multiplet determined in step (c) includes the second base type followed by the next base, thereby determining the presence of two series of base multiplets in the template nucleic acid. Optionally, the method can further include (h) repeating steps (a) through (f), wherein the nucleotide cognate of the third base type includes a reversible terminator, and wherein nucleotide cognates of the first, second and fourth base types in the mixture are extendible, and wherein the base multiplet determined in step (c) includes the third base type followed by the next base, thereby determining the presence of three series of base multiplets in the template nucleic acid. As a further option, the method can include (i) repeating steps (a) through (f), wherein the nucleotide cognate of the fourth base type includes a reversible terminator, and wherein nucleotide cognates of the first, second and third base types in the mixture are extendible, and wherein the base multiplet determined in step (c) includes the fourth base type followed by the next base, thereby determining the presence of four series of base multiplets in the template nucleic acid.

In another embodiment a method of characterizing a nucleic acid can include the steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid, wherein the mixture includes nucleotide cognates of first, second, third and fourth different base types, wherein the nucleotide cognate of the first base type has a reversible terminator, and wherein nucleotide cognates of the second, third and fourth base types are extendable; (b) contacting the extended primer hybrid with a nucleotide cognate for at least one of the different base types and a polymerase to form a stabilized ternary complex that includes the extended primer hybrid, the polymerase and a nucleotide cognate of the next base in the template; (c) detecting the stabilized ternary complex to distinguish the next base from other base types in the template; (d) determining the presence of a base multiplet in the template nucleic acid including the first base type followed by the next base; (e) repeating steps (a) through (c) using the extended primer hybrid as the primer-template nucleic acid hybrid and (f) determining the presence of a series of at least two base multiplets in the template nucleic acid, wherein the first region of the template is 3' to the series of at least two base multiplets. Optionally, the method further includes the step of (g) performing polymerase extension of the extended primer in a second sequencing process, wherein the second sequencing process detects signals indicative of a sequence of the template that is 5' to the series of at least two base multiplets.

The present disclosure provides a method of characterizing a nucleic acid that includes the steps of (a) contacting a primer-template nucleic acid hybrid with a polymerase and a mixture of nucleotides under conditions to produce an extended primer hybrid and to form a stabilized ternary complex that includes the extended primer hybrid, the polymerase and a nucleotide cognate of the next base in the template, wherein the mixture includes nucleotide cognates of first, second, third and fourth different base types, wherein the nucleotide cognate of the first base type comprises a reversible terminator, and wherein at least one of the nucleotide cognates of the second, third or fourth base types is extendable; (b) detecting the stabilized ternary complex to distinguish the next base from other base types in the template; and (c) determining the presence of a base multiplet in the template nucleic acid including the first base type followed by the next base. Optionally, the method includes steps of (d) repeating steps (a) and (b) using the extended primer hybrid as the primer-template nucleic acid hybrid; and (e) determining the presence of a series of at least two base multiplets in the template nucleic acid. In some embodiments, the nucleotide cognate of the first base type has a reversible terminator and the nucleotide cognates of the second, third and fourth base types are extendable. Alternatively, the nucleotide cognates of the first and second base types have a reversible terminator and the nucleotide cognates of the third and fourth base types are extendable.

In a further embodiment a method of characterizing a nucleic acid can include the steps of (a) contacting a primer-template nucleic acid hybrid with a polymerase and a mixture of nucleotides under conditions to produce an extended primer hybrid and to form a stabilized ternary complex that includes the extended primer hybrid, the polymerase and a nucleotide cognate of the next base in the template, wherein the mixture includes nucleotide cognates of first, second, third and fourth different base types, wherein the nucleotide cognate of the first base type comprises a reversible terminator, and wherein nucleotide cognates of the second, third and fourth base types are extendable; (b) detecting the stabilized ternary complex to distinguish the next base from other base types in the template; (c) determining the presence of a base multiplet in the template nucleic acid including the first base type followed by the next base; (d) repeating steps (a) and (b) using the extended primer hybrid as the primer-template nucleic acid hybrid; (e) determining the presence of a series of at least two base multiplets in the template nucleic acid; and (f) repeating steps (a) through (e), wherein the nucleotide cognate of the second base type has a reversible terminator, and wherein nucleotide cognates of the first, third and fourth base types in the mixture are extendible, and wherein the base multiplet determined in step (c) includes the second base type followed by the next base, thereby determining the presence of two series of base multiplets in the template nucleic acid. Optionally, the method can further include a step of (g) repeating steps (a) through (e), wherein the nucleotide cognate of the third base type has a reversible terminator, and wherein nucleotide cognates of the first, second and fourth base types in the mixture are extendible, and wherein the base multiplet determined in step (c) includes the third base type followed by the next base, thereby determining the presence of three series of base multiplets in the template nucleic acid. As a further option the method includes a step of (h) repeating steps (a) through (e), wherein the nucleotide cognate of the fourth base type has a reversible terminator, and wherein nucleotide cognates of the first, second and third base types in the mixture are extendible, and wherein the base multiplet determined in step (c) includes the fourth base type followed by the next base, thereby determining the presence of four series of base multiplets in the template nucleic acid.

In another embodiment a method of characterizing a nucleic acid can include the steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid and to form a stabilized ternary complex that includes the extended primer hybrid, the polymerase and a nucleotide cognate of the next base in the template, wherein the mixture includes nucleotide cognates of first, second, third and fourth different base types, wherein the nucleotide cognate of the first base type comprises a reversible terminator, and wherein nucleotide cognates of the second, third and fourth base types are extendable; (b) detecting the stabilized ternary complex to distinguish the next base from other base types in the template; (c) determining the presence of a base multiplet in the template nucleic acid including the first base type followed by the next base; and (d) repeating steps (a) and (b) using the extended primer hybrid as the primer-template nucleic acid hybrid; and (e) determining the presence of a series of at least two base multiplets in the template nucleic acid, wherein the first region of the template is 3' to the series of at least two base multiplets. Optionally, the method can include a step (f) performing polymerase extension of the extended primer in a second sequencing process, wherein the second sequencing process detects signals indicative of a sequence of the template that is 5' to the series of at least two base multiplets.

The present disclosure provides a method of characterizing a nucleic acid that includes the steps of (a) contacting a primer-template nucleic acid hybrid with a polymerase and a mixture of nucleotides under conditions to produce an extended primer hybrid, wherein the mixture includes nucleotide cognates of no more than three of four different base types; (b) further extending the extended primer hybrid with a nucleotide cognate of a fourth of the four different base types in the absence of the nucleotide cognates of (a), thereby producing a further extended primer hybrid; (c) forming a stabilized ternary complex that includes the further extended primer hybrid, a polymerase and a nucleotide cognate of the next base in the template; (d) detecting the stabilized ternary complex to distinguish the next base from other base types in the template; and (e) determining the presence of a base multiplet in the template nucleic acid including the fourth of the four different base types followed by the next base. Optionally, the method further includes steps of (f) repeating steps (a) through (d) using the further extended primer hybrid as the primer-template nucleic acid hybrid and (g) determining the presence of a series of at least two base multiplets in the template nucleic acid.

In a further embodiment a method of characterizing a nucleic acid can include the steps of (a) contacting a primer-template nucleic acid hybrid with a polymerase and a mixture of nucleotides under conditions to produce an extended primer hybrid, wherein the mixture includes nucleotide cognates of no more than three of four different base types; (b) further extending the extended primer hybrid with a nucleotide cognate of a fourth of the four different base types in the absence of the nucleotide cognates of (a), thereby producing a further extended primer hybrid; (c) forming a stabilized ternary complex that includes the further extended primer hybrid, a polymerase and a nucleotide cognate of the next base in the template; (d) detecting the stabilized ternary complex to distinguish the next base from other base types in the template; (e) determining the presence of a base multiplet in the template nucleic acid including the fourth of the four different base types followed by the next base; (f) repeating steps (a) through (d) using the further extended primer hybrid as the primer-template nucleic acid hybrid; (g) determining the presence of a series of at least two base multiplets in the template nucleic acid; and (h) repeating steps (a) through (g), wherein the nucleotide cognate of the fourth base type is replaced with a nucleotide cognate of a first base type and wherein nucleotide cognates of the first base type are not used in step (a), thereby determining the presence of two series of base multiplets in the template nucleic acid. Optionally, the method can further include (i) repeating steps (a) through (g), wherein the nucleotide cognate of the fourth base type is replaced with a nucleotide cognate of a second base type and wherein nucleotide cognates of the second base type are not used in step (a), thereby determining the presence of three series of base multiplets in the template nucleic acid. As a further option the method can include (j) repeating steps (a) through (g), wherein the nucleotide cognate of the fourth base type is replaced with a nucleotide cognate of a third base type and wherein nucleotide cognates of the third base type are not used in step (a), thereby determining the presence of four series of base multiplets in the template nucleic acid.

In another embodiment a method of characterizing a nucleic acid can include the steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid, wherein the mixture includes nucleotide cognates of no more than three of four different base types; (b) further extending the extended primer hybrid with a nucleotide cognate of a fourth of the four different base types in the absence of the nucleotide cognates of (a), thereby producing a further extended primer hybrid; (c) forming a stabilized ternary complex that includes the further extended primer hybrid, a polymerase and a nucleotide cognate of the next base in the template; (d) detecting the stabilized ternary complex to distinguish the next base from other base types in the template; (e) determining the presence of a base multiplet in the template nucleic acid including the fourth of the four different base types followed by the next base; (f) repeating steps (a) through (d) using the further extended primer hybrid as the primer-template nucleic acid hybrid; and (g) determining the presence of a series of at least two base multiplets in the template nucleic acid, wherein the first region of the template is 3' to the series of at least two base multiplets. Optionally, the method can include a step (h) performing polymerase extension of the extended primer in a second sequencing process, wherein the second sequencing process detects signals indicative of a sequence of the template that is 5' to the series of at least two base multiplets.

The details of one or more embodiments are set forth in the accompanying drawings and the description below. Other features, objects, and advantages will be apparent from the description and drawings, and from the claims.

DETAILED DESCRIPTION

Figure 1:
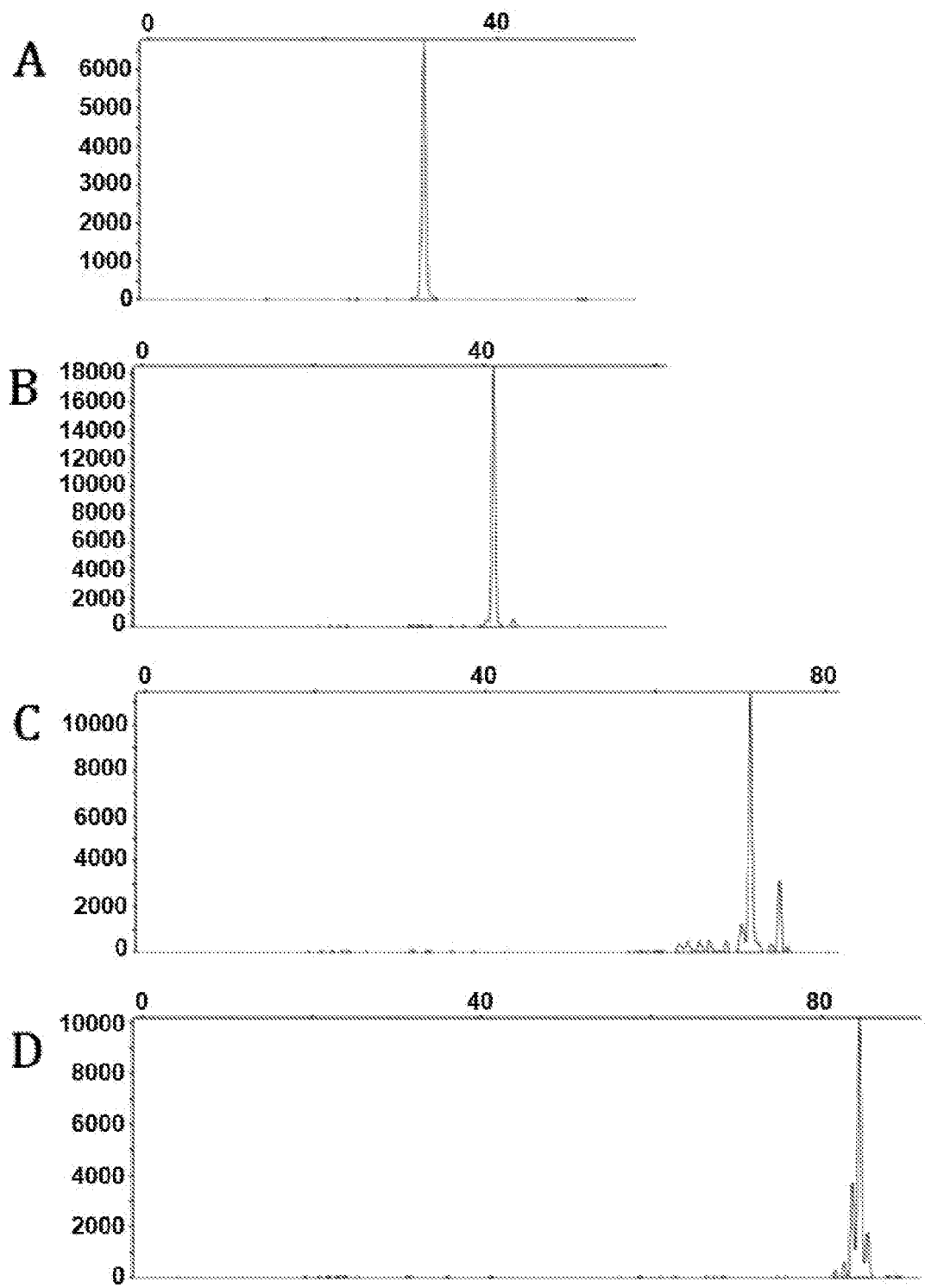
FIG. 1 shows capillary electrophoresis traces for a non-extended primer from the Tough-22 (SEQ ID NO:1) primer-template hybrid (FIG. 1A); for the primer after 10 SBB™ cycles that employ 4 reversible terminator nucleotides during the extension step (FIG. 1B); for the primer after 10 SBB™ cycles that employ a dT-aminooxy, reversible terminator nucleotide and 3 natural nucleotides during the extension step (FIG. 1C); and for the primer after 10 SBB™ cycles that employ 4 natural nucleotides during the extension step (FIG. 1D).

Many nucleic acid sequencing techniques, such as fluorescence-based Sequencing By Binding™ (SBB™) technology, use light irradiation during detection. An undesirable repercussion of light-based detection is that repeated or extended periods of light irradiation can produce side products or artifacts that interfere with the reaction. For example, photo-oxidation can render the nucleic acids incapable of proceeding in the sequencing reaction due to crosslinking to other components or via fragmentation. The cumulative impacts of radiation can adversely limit sequencing read length and throughput.

The present disclosure provides methods that can be used to increase read length by reducing the number of reaction cycles to which the nucleic acids are exposed. Fewer cycles means less exposure of the nucleic acids to light and potentially damaging chemicals. SBB™ technology has a unique property, compared to other sequencing methods, of being able to separate primer extension and nucleotide detection into two steps. Typically, the SBB™ technique incrementally detects each position in a template since one nucleotide is added to the primer during the extension step of each cycle and the next correct nucleotide is then detected before the next cycle begins. In this case, the number of cycles is equivalent to the length of the read.

In particular configurations of the methods set forth herein, a primer extension step is carried out such that the number of nucleotides added to the primer is not necessarily known or determined; however, the type of nucleotide at the 3' end of the primer, or the type of nucleotide that is adjacent to the 3' end of the primer, is known or capable of being determined. The nucleotide type can be determined from the composition of the nucleotide mixture used during extension without any need to detect the extension product. For example, the mixture of nucleotides can include four different base types, wherein nucleotides of a first base type have a reversible terminator and the other three nucleotide types are extendable. In this case, the extension product will have at its 3' end a nucleotide having the first base type. In another example, the mixture of nucleotides can include only three of the four different base types that are expected to have complementary bases in the template. The extension product will not extend beyond a template position that complements the omitted base type. In both of these examples, the length of extension products produced from multiple cycles will be variable and, in many cases, unknown. However, the number of nucleotides of a particular type that end up in the extension product can be determined from the number of cycles performed. The nucleotide count can provide useful information about the composition of the nucleic acid template; information that can be used, for example, as a signature for the template or, in combination with other information, to determine the sequence of the template.

In particular configurations of the present methods, the extension step of a sequencing procedure is modified such that a variable number of nucleotides is added during each cycle and then the next correct nucleotide is detected. As set forth below, the extension can be carried out in a way that the type of nucleotide at the 3' end of the primer is known. The net result is that detecting the next correct nucleotide during each cycle allows identification of a dinucleotide containing the nucleotide at the primer 3' end and the detected nucleotide. Repeating the steps identifies a series of dinucleotides, wherein the number and type of nucleotides in the template that separates each dinucleotide is not necessarily known. Since some extension steps will incorporate more than one nucleotide, the series of dinucleotides may span a length of template that is longer than the number of cycles performed. The series of dinucleotides provides a low-resolution signature sequence for the template.

A dinucleotide is one type of base multiplet that can be identified and used in a method of the present disclosure. Longer base multiplets can be identified for a particular template nucleic acid by following the above-described variable length extension step with more than one cycle of examination and single nucleotide extension. For example, a trinucleotide can be identified by first performing a variable length extension step in a way that the type of nucleotide at the 3' end of the extended primer is known (i.e. the first nucleotide in the trinucleotide), secondly performing a cycle that includes examination of a next correct nucleotide (i.e. the second nucleotide in the trinucleotide) and extension of the primer by a single nucleotide, and thirdly performing an examination step of a next correct nucleotide for the extended primer (i.e. the third nucleotide in the trinucleotide). Accordingly, a base multiplet of any of a variety of lengths can form the basis for a signature that characterizes the template nucleic acid.

In particular embodiments, a higher resolution signature sequence can be obtained by combining low resolution signatures obtained from the same template nucleic acid. Specifically, the extended primer produced in the previous sequencing run can be removed from the template and the variable extension SBB™ technique can be repeated. However, in the repeated run the variable extension step will be configured to cap the primer with a different nucleotide type than the type used in the previous sequencing run. As set forth in further detail below, three or four base multiplet series (each generated with a different type of primer capping nucleotide) can be combined to arrive at a sequence for the template that is determined at single-base resolution.

In particular embodiments, the methods of the present disclosure employ an extension step that uses mixtures of nucleotides that will stop at a particular type of base in a template. For example, the mixture used for extension can include extendible nucleotides that pair with three types of bases in the template and a reversibly terminated nucleotide that pairs with a fourth base type in the template. The extension step will produce an extended primer having the cognate of the fourth base type at its 3' end. Thus, the identity of the nucleotide at the 3' end of the extended primer can be deduced from the nucleotide composition of the extension mixture. The next correct nucleotide in the template can be detected via formation of a stabilized ternary complex at the end of the extended primer. The extended primer can then be deblocked and the cycle repeated to determine a series of dinucleotides present in the template.

Alternatively, a mixture of nucleotides used in an extension step can include cognate nucleotides for only three types of bases in the template (i.e. omitting cognate nucleotides for a fourth type of base in the template). The type of nucleotide at the 3' end of the extended primer may not necessarily be known. However, the identity of the next correct nucleotide can be deduced from the nucleotide composition of the extension mixture. In this example, the next template base is the fourth type of base. Subsequent extension using only cognate nucleotide for the fourth base type will result in an extended primer that is known to have the cognate of the fourth base type at its 3' end. The next correct nucleotide, or next template base, can be detected via formation of a stabilized ternary complex at the end of the extended primer. The extended primer need not be terminated. Rather, stability can be provided to the ternary complex via absence of a catalytic metal needed by the polymerase for extension, presence of a polymerase inhibitor such as a non-catalytic metal, or use of a polymerase variant that forms a ternary complex but is incapable of catalyzing primer extension. Alternatively, the cognate nucleotide at the 3' end of the primer can include a reversible terminator that provides stability to the ternary complex. In this case, the reversibly terminated primer can then be deblocked to extend the dinucleotide to a longer multiplet and/or to allow the cycle to be repeated.

Particular embodiments of the methods set forth herein identify one or more base multiplet series that can be used as a signature to identify nucleic acid sequences. For example, a signature dinucleotide series can be determined for a target nucleic acid and the signature can be compared to a signature for a known nucleic acid sequence to confirm or dismiss the target nucleic acid as having the same sequence as the known nucleic acid. An advantage of such signatures is that they can be obtained more quickly than a full sequence, thereby allowing rapid identification of the target nucleic acid. A further advantage is that the length of a genome spanned by the signature will typically be longer than the length spanned by a standard run, and the information imparted by the signature can provide long range genomic structural information that is not provided by the shorter reads produced from the same number of cycles for a standard run.

In some embodiments, a single-base resolution sequence can be determined for a first region of a target nucleic acid and a signature can be obtained for a second region of the target nucleic acid. The signature can be, for example, a series of base multiplets or a count of nucleotides of a particular type. The target can then be aligned with a longer sequence (e.g. a genome fragment can be aligned with the genome) by aligning not only the single base resolution region of the sequence but also the signature region. The added information from the signature region provides further information for aligning reads. The signature can be a tail that is appended to a high resolution read, for example, by performing variable extension SBB™ technique on a primer that was previously extended in a standard SBB™ technique (or vice versa). Similarly, the variable extension SBB™ technique can be performed to produce a signature linker between two single-base resolution reads. The resulting sequence can be aligned as a "paired read" wherein the signature for the linker is used along with the single-base resolution reads for alignment to a reference sequence. The linker signature can add alternative or additional information to standard paired read alignment techniques (also referred to in the art as "paired end" alignment techniques), in which only distance of the linker enters into the alignment determination. Specifically, the paired reads can be aligned to a reference genome based not only on proximity of alignment for the two reads in the reference, but also based on comparison of the observed signature region to the region of the reference that intervenes the regions that align to the two reads. For example, the count of a particular type of nucleotide in the observed signature can be compared to the count in the relevant region of the reference sequence, or the series of base multiplets in the observed signature can be compared to the series in the relevant region of the reference sequence.

In another paired read configuration, the number of nucleotides in a linker region can be empirically determined and used as a signature for the linker region. More specifically, a first region of a template nucleic acid can be sequenced by extending a primer along the template using a single-base resolution technique, the extended primer can then be further extended along a second region of the template using a 'dark' extension technique, and then the further extended primer can be extended even further along a third region of the template using a single-base resolution technique. Dark extension can be achieved by repeated cycles of primer extension, wherein each of the cycles does not include detection steps that would otherwise be used to observe primer extension products. For example, each dark extension cycle can employ one or more steps set forth herein for achieving primer extension in an SBB' technique, but each cycle can omit detection steps set forth herein or otherwise known in the art. Each dark extension cycle can use nucleotide cognates for all base types expected to be in the template (e.g. cognates for all four base types expected to be in native genomic DNA). Since they will not be detected, the nucleotide cognates need not be labeled. However, the nucleotide cognates can contain reversible terminators, in which case each cycle can include a deblocking step. In this exemplary configuration, the number of dark extension cycles performed will correlate with the length of the second region of the template (i.e. the number of bases in the second region), and this empirically determined length will in turn provide a signature for the linker region between the first and third regions that are sequenced by single base resolution techniques. The single-base resolution techniques can be the same or different for the first and third regions. Optionally, one or both of the single-base resolution techniques can be an SBB™ technique.

Terms used herein will be understood to take on their ordinary meaning in the relevant art unless specified otherwise. Several terms used herein, and their meanings, are set forth below.

As used herein, the term "adjacent," when used in reference to two nucleotides in a nucleic acid molecule or sequence, means one of the nucleotides immediately follows the other nucleotide in the molecule or sequence. Accordingly, adjacent nucleotides are covalently linked to each other in the nucleic acid molecule. In contrast, two nucleotides that are near each other can, optionally, be separated by one or a few intervening nucleotides in the nucleic acid molecule or sequence.

As used herein, the term "aligning," when used in reference to nucleic acid sequences, means comparing two or more sequences to identify regions of similarity. Aligned sequences can be represented as separate rows in a matrix. A particular sequence (or row in a matrix) can have one or more gaps when aligned to another sequence (or row in the matrix). A gap can represent, for example, one or more positions in the gapped sequence that are unknown, ambiguous or absent. For example, a first sequence can be represented as a series of base multiplets in which gaps may separate two or more base multiplets when the first sequence is aligned to a reference sequence. In this example, each gap may separate one base multiplet from another when the first sequence is aligned to the reference sequence.

As used herein, the term "array" refers to a population of molecules that are attached to one or more solid-phase substrates such that the molecules at one feature can be distinguished from molecules at other features. An array can include different molecules that are each located at different addressable features on a solid-phase substrate. Alternatively, an array can include separate solid-phase substrates each functioning as a feature that bears a different molecule, wherein the different molecules can be identified according to the locations of the solid-phase substrates on a surface to which the solid-phase substrates are attached, or according to the locations of the solid-phase substrates in a liquid such as a fluid stream. The molecules of the array can be, for example, nucleotides, nucleic acid primers, nucleic acid templates or nucleic acid enzymes such as polymerases, ligases, exonucleases or combinations thereof.

As used herein, the term "base multiplet" refers to at least two adjacent bases in a nucleic acid sequence or at least two nucleotides that are attached to each other via 5' to 3' phosphodiester linkage. Generally, the nucleotides of a base multiplet are listed in the 5' to 3' direction (e.g. 5'GT3' is generally referred to as a GT dinucleotide, unless another convention is specified). Exemplary base multiplets include, for example, a dinucleotide, which contains two adjacent bases or nucleotides; a trinucleotide, which contains three adjacent bases or nucleotides; a tetranucleotide, which contains four adjacent nucleotides or bases, etc. Each base in a multiplet can be unambiguously identified as a particular base type (e.g. A, C, T or G). Alternatively, a base in a multiplet can be degenerate, for example, being identified as R (i.e. A or G), M (i.e. A or C), W (i.e. A or T), S (i.e. C or G), Y (i.e. C or T), K (i.e. G or T), B (i.e. C or G or T), D (i.e. A or G or T), H (i.e. A or C or T), V (i.e. A or C or G), or N (i.e. A or C or G or T).

As used herein, the term "blocking moiety," when used in reference to a nucleotide, means a part of the nucleotide that inhibits or prevents the 3' oxygen of the nucleotide from forming a covalent linkage to a next correct nucleotide during a nucleic acid polymerization reaction. The blocking moiety of a "reversible terminator" nucleotide can be removed from the nucleotide analog, or otherwise modified, to allow the 3'-oxygen of the nucleotide to covalently link to a next correct nucleotide. Such a blocking moiety is referred to herein as a "reversible terminator moiety." Exemplary reversible terminator moieties are set forth in U.S. Pat. Nos. 7,427,673; 7,414,116; 7,057,026; 7,544,794 or 8,034,923; or PCT publications WO 91/06678 or WO 07/123744, each of which is incorporated herein by reference. A nucleotide that has a blocking moiety or reversible terminator moiety can be at the 3' end of a nucleic acid, such as a primer, or can be a monomer that is not covalently attached to a nucleic acid.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extension," when used in reference to a nucleic acid, means a process of adding at least one nucleotide to the 3' end of the nucleic acid. The term "polymerase extension," when used in reference to a nucleic acid, refers to a polymerase catalyzed process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "extendable," when used in reference to a nucleotide, means that the nucleotide has an oxygen or hydroxyl moiety at the 3' position, and is capable of forming a covalent linkage to a next correct nucleotide if and when incorporated into a nucleic acid. An extendable nucleotide can be at the 3' position of a primer or it can be a monomeric nucleotide. A nucleotide that is extendable will lack blocking moieties such as reversible terminator moieties.

As used herein, the term "extended primer hybrid" refers to a primer-template nucleic acid hybrid following incorporation of at least one nucleotide to the primer. The incorporation event can be, for example, polymerase catalyzed addition of one or more nucleotides to the 3' end of the primer.

As used herein, the term "feature," when used in reference to an array, means a location in an array where a particular molecule is present. A feature can contain only a single molecule or it can contain a population of several molecules of the same species (i.e. an ensemble of the molecules). Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 microns, 50 microns, 10 microns, 5 microns, 1 micron, or 0.5 micron. Alternatively or additionally, an array can have features that are separated by greater than 0.5 micron, 1 micron, 5 microns, 10 microns, 50 microns or 100 microns. The features can each have an area of less than 1 square millimeter, 500 square microns, 100 square microns, 25 square microns, 1 square micron or less.

As used herein, the term "label" refers to a molecule or moiety thereof that provides a detectable characteristic. The detectable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like.

As used herein, the term "next correct nucleotide" refers to the nucleotide type that will bind and/or incorporate at the 3' end of a primer to complement a base in a template strand to which the primer is hybridized. The base in the template strand is referred to as the "next base" and is immediately 5' of the base in the template that is hybridized to the 3' end of the primer. The next correct nucleotide can be referred to as the "cognate" of the next base and vice versa. Cognate nucleotides that interact with each other in a ternary complex or in a double stranded nucleic acid are said to "pair" with each other. A nucleotide having a base that is not complementary to the next template base is referred to as an "incorrect", "mismatch" or "non-cognate" nucleotide.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or non-natural analogs thereof such as dideoxyribonucleotide triphosphates (ddNTPs) or reversibly terminated nucleotide triphosphates (rtNTPs).

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the term "primer-template nucleic acid hybrid" or "primer-template hybrid" refers to a nucleic acid hybrid having a double stranded region such that one of the strands has a 3'-end that can be extended by a polymerase. The two strands can be parts of a contiguous nucleic acid molecule (e.g. a hairpin structure) or the two strands can be separable molecules that are not covalently attached to each other.

As used herein, the term "primer" refers to a nucleic acid having a sequence that binds to a nucleic acid at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof.

As used herein, the term "series of base multiplets" refers to a representation of the relative order for particular base multiplets in a sequence. The base multiplets in the series can be the same as each other or different from each other. For example, the dinucleotides in a series can differ from each other due to variability in the type of nucleotide that is present at the 3' position of the dinucleotide, at the 5' position of the dinucleotide or both. In some embodiments, the dinucleotides in a series can differ from each other due to variability in the type of nucleotide that is present at the 3' position while the nucleotide type at the 5' position is uniform. Alternatively, the dinucleotides in a series can have a uniform type of nucleotide at the 3' position while being variable with regard to the nucleotide type at the 5' position. Similarly, longer base multiplets can be uniform at one position and variable at other positions. One of the positions in a multiplet can be degenerate for 2 or more nucleotide types. Taking IUPAC symbols as an example, one of the positions can be identified as R (i.e. A or G), M (i.e. A or C), W (i.e. A or T), S (i.e. C or G), Y (i.e. C or T), K (i.e. G or T), B (i.e. C or G or T), D (i.e. A or G or T), H (i.e. A or C or T), V (i.e. A or C or G) or N (i.e. A or C or G or T). The base multiplets in a series need not be contiguous when aligned with a reference sequence. Accordingly, two base multiplets in a series can be separated by gaps when aligned with the reference sequence.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, the term "type" is used to identify molecules that share the same chemical structure. For example, a mixture of nucleotides can include several dCTP molecules. The dCTP molecules will be understood to be the same type as each other, but a different type compared to dATP, dGTP, dTTP etc. Similarly, individual DNA molecules that have the same sequence of nucleotides are the same type, whereas DNA molecules with different sequences are different types. The term "type" can also identify moieties that share the same chemical structure. For example, the cytosine bases in a template nucleic acid will be understood to be the same type of base as each other independent of their position in the template sequence.

The embodiments set forth below and recited in the claims can be understood in view of the above definitions.

The present disclosure provides a method of characterizing a nucleic acid. The method can include the steps of (a) contacting a primer-template nucleic acid hybrid with a polymerase and a mixture of nucleotides under conditions to produce an extended primer hybrid, wherein the mixture includes nucleotide cognates of first, second, third and fourth different base types, wherein the nucleotide cognate of the first base type has a reversible terminator, and wherein at least one of the nucleotide cognates of the second, third or fourth base types is extendable; (b) contacting the extended primer hybrid with a nucleotide cognate for at least one of the different base types and a polymerase to form a stabilized ternary complex that includes the extended primer hybrid, the polymerase and a nucleotide cognate of the next base in the template; (c) detecting the stabilized ternary complex to distinguish the next base from other base types in the template; and (d) determining the presence of a base multiplet in the template nucleic acid including the first base type followed by the next base. Optionally, the method further includes steps of (e) repeating steps (a) through (c) using the extended primer hybrid as the primer-template nucleic acid hybrid and (f) determining the presence of a series of at least two base multiplets in the template nucleic acid. In embodiments, prior to step (e), the method further includes removing the reversible terminator from the extended primer.

Also provided is a method of characterizing a nucleic acid that includes steps of (a) contacting a primer-template nucleic acid hybrid with a polymerase and a mixture of nucleotides under conditions to produce an extended primer hybrid and to form a stabilized ternary complex that includes the extended primer hybrid, the polymerase and a nucleotide cognate of the next base in the template, wherein the mixture includes nucleotide cognates of first, second, third and fourth different base types, wherein the nucleotide cognate of the first base type comprises a reversible terminator, and wherein at least one of the nucleotide cognates of the second, third or fourth base types is extendable; (b) detecting the stabilized ternary complex to distinguish the next base from other base types in the template; and (c) determining the presence of a base multiplet in the template nucleic acid including the first base type followed by the next base. Optionally, the method includes steps of (d) repeating steps (a) and (b) using the extended primer hybrid as the primer-template nucleic acid hybrid; and (e) determining the presence of a series of at least two base multiplets in the template nucleic acid.

The present disclosure further provides a method of characterizing a nucleic acid that includes steps of (a) contacting a primer-template nucleic acid hybrid with a polymerase and a mixture of nucleotides under conditions to produce an extended primer hybrid, wherein the mixture includes nucleotide cognates of no more than three of four different base types; (b) further extending the extended primer hybrid with a nucleotide cognate of a fourth of the four different base types in the absence of the nucleotide cognates of (a), thereby producing a further extended primer hybrid; (c) forming a stabilized ternary complex that includes the further extended primer hybrid, a polymerase and a nucleotide cognate of the next base in the template; (d) detecting the stabilized ternary complex to distinguish the next base from other base types in the template; and (e) determining the presence of a base multiplet in the template nucleic acid including the fourth of the four different base types followed by the next base. Optionally, the method further includes steps of (f) repeating steps (a) through (d) using the further extended primer hybrid as the primer-template nucleic acid hybrid and (g) determining the presence of a series of at least two base multiplets in the template nucleic acid.

Nucleic acids that are used in a method or composition herein can be DNA such as genomic DNA, synthetic DNA, amplified DNA, copy DNA (cDNA) or the like. RNA can also be used such as mRNA, ribosomal RNA, tRNA or the like. Nucleic acid analogs can also be used as templates herein. Thus, template nucleic acids used herein can be derived from a biological source, synthetic source or amplification product. Primers used herein can be DNA, RNA or analogs thereof.

Particularly useful nucleic acid templates are genome fragments that include sequences identical to a portion of a genome. A population of genome fragments can include at least 5%, 10%, 20%, 30%, or 40%, 50%, 60%, 70%, 75%, 80%, 85%, 90%, 95% or 99% of a genome. A genome fragment can have, for example, a sequence that is substantially identical to at least about 25, 50, 70, 100, 200, 300, 400, 500, 600, 700, 800, 900 or 1000 or more nucleotides of a genome. Alternatively or additionally, a genome fragment can have a sequence that is substantially identical to no more than $1\times10^5$, $1\times10^4$, $1\times10^3$, 800, 600, 400, 200, 100, 75, 50 or 25 nucleotides of a genome. A genome fragment can be DNA, RNA, or an analog thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual,* 3rd edition, Cold Spring Harbor Laboratory, N.Y. (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. Nos. 6,355,431 or 9,045,796, each of which is incorporated herein by reference. Amplification can also be carried out using a method set forth in Sambrook et al., *Molecular Cloning: A Laboratory Manual,* 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A method of the present disclosure can include a step of contacting a primer-template nucleic acid hybrid with a polymerase and a mixture of nucleotides under conditions to produce an extended primer hybrid. One or more of the nucleotides in the mixture can be reversibly terminated. For example, at least 1, 2, 3, 4 or more nucleotide types in the mixture can be reversibly terminated. Alternatively or additionally, at most 4, 3, 2, or 1 nucleotide types in the mixture can be reversibly terminated. Similarly, one or more nucleotide types that are reversibly terminated in the mixture can be complementary to at least 1, 2, 3 or 4 base types in a template nucleic acid. Alternatively or additionally, the reversibly terminated nucleotide types in the mixture can be complementary to at most 4, 3, 2, or 1 base types in a template nucleic acid. Reversibly terminated and non-terminated nucleotides can be present simultaneously in an extension reaction. For example, some or all of the nucleotide types can be delivered simultaneously in a single extension reaction. Alternatively, different nucleotide types can be serially delivered (individually or in subsets) such that they are combined into a single extension reaction. The nucleotide types can have base moieties selected from those set forth herein such as those found in native DNA or RNA, or analogs thereof.

Adding a reversibly terminated nucleotide to the 3' end of a primer provides a means to prevent a subsequent nucleotide from being added to the primer during the extension step and further prevents unwanted extension of the primer in a subsequent examination step. Thus, a position in a template that is adjacent to a nucleotide of a particular type can be examined. In such embodiments, a stabilized ternary complex can be formed at the position and examined to detect the next correct nucleotide for the template that is hybridized to the extended, reversibly terminated primer. The method can be repeated in a step-wise fashion by then removing or modifying the reversible terminator moiety from the extended, reversibly terminated primer to produce an extendible primer.

Typically, a reversibly terminated nucleotide that is added to a primer in a method set forth herein does not have an exogenous label. This is because the extended primer need not be detected in a method set forth herein. However, if desired, one or more types of reversibly terminated nucleotides used in a method set forth herein can be detected, for example, via exogenous labels attached to the nucleotides.

Exemplary reversible terminator moieties, methods for incorporating them into primers and methods for modifying the primers for further extension (often referred to as 'deblocking') are set forth in U.S. Pat. Nos. 7,544,794; 7,956,171; 8,034,923; 8,071,755; 8,808,989; or 9,399,798. Further examples are set forth in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; and 7,405,281, and US 2008/0108082, each of which is incorporated herein by reference.

As set forth above, reversibly terminated nucleotides provide a means to stop extension at a particular base type in a template nucleic acid. Another means to achieve this type of control over extension is to perform extension using a mixture of nucleotides that lacks nucleotide types that are capable of pairing with one or more type of nucleotide expected to be present in the template nucleic acid. For example, a mixture of nucleotides used for extension can lack at least 1, 2 or 3 types of nucleotides that are expected to pair with bases in the template. Alternatively or additionally, at most 3, 2, or 1 of the nucleotide types can be absent in the mixture. Similarly, the mixture can include nucleotides that are complementary to no more than 3, 2 or 1 base types expected to be present in a template nucleic acid. Alternatively or additionally, the mixture includes nucleotides that are complementary to at least 1, 2 or 3 of the base types expected to be present in a template nucleic acid. The different nucleotide types can be present simultaneously in an extension reaction, or they can participate in serial extension reactions. For example, some or all of the nucleotide types can be delivered simultaneously in a single extension reaction. Alternatively, different nucleotide types can be serially delivered (individually or in subsets) such that they are combined into a single extension reaction or such that serial extension reactions occur. The nucleotide types can have base moieties selected from those set forth herein such as those found in native DNA or RNA, or analogs thereof.

A primer extension step can be carried out by contacting a primer-template nucleic acid hybrid with an extension reaction mixture. Typically, fluid that was present in a previous examination step is removed and replaced with the extension reaction mixture. Alternatively, the extension reaction mixture can be formed by adding one or more reagents to the fluid that was present in the examination step. Optionally, the extension reaction mixture includes a different composition of nucleotides than an examination step. For example, an examination step can include one or more nucleotide types that are not present in the extension reaction and vice versa. By way of more specific example, an extension step can omit at least one type of nucleotide and an examination step can employ at least four types of nucleotides. Optionally, one or more nucleotide types is added to an examination mixture for a primer extension step.

Nucleotides present in an examination step may cause unwanted nucleotide incorporation if carried over into an extension step. Thus, a wash step can be employed prior to a primer extension step to remove nucleotides. Optionally, free nucleotides may be removed by enzymes, such as a phosphatase, apyrase or hexokinase; by chemical modification; or by physical separation techniques such as liquid-phase extraction, solid phase extraction or electrophoretic separation.

In some embodiments, reagents for extension and examination can be simultaneously present. For example, a reaction mixture can include polymerase, primer-template hybrid, reversibly terminated nucleotide that is cognate to one type of base expected to be in the template and extendable nucleotides that are cognates for the other three types of base expected to be in the template. In this case, primer extension will occur until the reversibly terminated nucleotide is incorporated and a ternary complex will form at the terminated end of the extended primer. The ternary complex will include one of the four nucleotides that is an appropriate next correct nucleotide. The ternary complex can be detected via labels on nucleotides, polymerase or both. For example, labels can be present on the 5' position of the nucleotides, such that the label is removed from any nucleotide that is incorporated into the primer during extension, but is retained for any nucleotide that participates in ternary complex formation. Thus, the ternary complex can be detected while avoiding unwanted signal from incorporated nucleotides.

A primer extension step need not use a labeled polymerase. For example, a polymerase that is used for an extension step need not be attached to an exogenous label (e.g. covalently or otherwise). Alternatively, a polymerase that is used for primer extension can include an exogenous label, for example, a label that was used in a previous examination step.

A method of this disclosure can include an examination step wherein ternary complex is formed and detected. Embodiments of the methods exploit the specificity with which a polymerase can form a stabilized ternary complex with a primer-template nucleic acid hybrid and a next correct nucleotide. The next correct nucleotide can be non-covalently bound to the stabilized ternary complex, interacting with the other members of the complex solely via non-covalent interactions. Useful methods and compositions for forming a stabilized ternary complex are set forth in further detail below and in commonly owned U.S. Pat. App. Pub. No. 2017/0022553 A1 or U.S. patent application Ser. No. 15/677,870 (published as US 2018/0044727 A1); US 2018/0187245 A1 (which claims priority to U.S. Pat. App. Ser. No. 62/440,624) or US 2018/0208983 A1 (which claims priority to U.S. Pat. App. Ser. No. 62/450,397), each of which is incorporated herein by reference.

Typically, the examination step is separate from the extension step, for example, due to reagent exchange between the steps. However, as set forth above, the extension and examination steps can occur in the same mixture in some embodiments.

While a ternary complex can form between a polymerase, primer-template nucleic acid hybrid and next correct nucleotide in the absence of certain catalytic metal ions (e.g., $Mg^{2+}$), chemical addition of the nucleotide is inhibited in the absence of the catalytic metal ions. Low or deficient levels of catalytic metal ions, causes non-covalent sequestration of the next correct nucleotide in a stabilized ternary complex. Other methods disclosed herein also can be used to produce a stabilized ternary complex.

Optionally, a stabilized ternary complex can be formed when the primer of the primer-template nucleic acid hybrid includes a blocking moiety (e.g. a reversible terminator moiety) that precludes enzymatic incorporation of an incoming nucleotide into the primer. The interaction can take place in the presence of stabilizers, whereby the polymerase-nucleic acid interaction is stabilized in the presence of the next correct nucleotide. The primer of the primer-template nucleic acid hybrid optionally can be either an extendible primer, or a primer blocked from extension at its 3'-end (e.g., blocking can be achieved by the presence of a reversible terminator moiety on the 3'-end of the primer). The primer-template nucleic acid hybrid, the polymerase and the cognate nucleotide are capable of forming a stabilized ternary complex when the base of the cognate nucleotide is complementary to the next base of the primer-template nucleic acid hybrid.

As set forth above, conditions that favor or stabilize a ternary complex can be provided by the presence of a blocking group that precludes enzymatic incorporation of an incoming nucleotide into the primer (e.g. a reversible terminator moiety on the 3' nucleotide of the primer) or the absence of a catalytic metal ion. Other useful conditions include the presence of a ternary complex stabilizing agent such as a non-catalytic ion (e.g., a divalent or trivalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide) are provided by the presence of one or more monovalent cations and/or glutamate anions. As a further option, a polymerase engineered to have reduced catalytic activity or reduced propensity for binary complex formation can be used.

As set forth above, ternary complex stabilization conditions can accentuate the difference in affinity of polymerase toward primer-template nucleic acid hybrids in the presence of different nucleotides, for example, by destabilizing binary complexes. Optionally, the conditions cause differential affinity of the polymerase for the primer-template in the presence of different nucleotides. By way of example, the conditions include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate ions. Optionally, the source of glutamate ions can be potassium glutamate. In some instances, the concentrations of potassium glutamate that can be used to alter polymerase affinity of the primer-template hybrid extend from 10 mM to 1.6 M of potassium glutamate, or any amount in between 10 mM and 1.6 M. As indicated above, high salt refers to a concentration of salt from 50 to 1,500 mM salt.

It will be understood that options set forth herein for stabilizing a ternary complex need not be mutually exclusive and instead can be used in various combinations. For example, a ternary complex can be stabilized by one or a combination of means including, but not limited to, crosslinking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, absence of catalytic metal ions, presence of a blocking moiety on the primer, and other means set forth herein.

A stabilized ternary complex can include a native nucleotide, nucleotide analog or modified nucleotide as desired to suit a particular application or configuration of the methods. Optionally, a nucleotide analog has a nitrogenous base, five-carbon sugar, and phosphate group, wherein any moiety of the nucleotide may be modified, removed and/or replaced as compared to a native nucleotide. Nucleotide analogs may be non-incorporable nucleotides (i.e. nucleotides that are incapable of reacting with the 3' oxygen of a primer to form a covalent linkage). Such nucleotides that are incapable of incorporation include, for example, monophosphate and diphosphate nucleotides. In another example, the nucleotide may contain modification(s) to the triphosphate group that make the nucleotide non-incorporable. Examples of non-incorporable nucleotides may be found in U.S. Pat. No. 7,482,120, which is incorporated by reference herein. In some embodiments, non-incorporable nucleotides may be subsequently modified to become incorporable. Non-incorporable nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, or caged nucleotides. Examples of nucleotide analogs are described in U.S. Pat. No. 8,071,755, which is incorporated by reference herein.

Nucleotide analogs that participate in stabilized ternary complexes can include terminators that reversibly prevent subsequent nucleotide incorporation at the 3'-end of the primer after the analog has been incorporated into the primer. For example, U.S. Pat. Nos. 7,544,794 and 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include those described in references cited elsewhere herein or in U.S. Pat. Nos. 7,956,171, 8,071,755, and 9,399,798 (the disclosures of these U.S. patents are incorporated herein by reference). In certain embodiments, a reversible terminator moiety can be removed from a primer, in a process known as "deblocking," allowing for subsequent nucleotide incorporation. Compositions and methods for deblocking are set forth in references cited herein in the context of reversible terminators. Other exemplary terminator moieties that can be attached to a 3' oxygen include —CH$_2$N$_3$ (methyl azide), —CH$_2$CH=CH$_2$, photoreactive moieties, or other moieties set forth in Chen et al. *Genomics, Proteomics & Bioinformatics* 11: 34-40 (2013), which is incorporated herein by reference, or other references incorporated by reference herein.

Alternatively, nucleotide analogs irreversibly prevent nucleotide incorporation at the 3'-end of the primer to which they have been incorporated. Irreversible nucleotide analogs include 2', 3'-dideoxynucleotides (ddNTPs such as ddGTP, ddATP, ddTTP, ddCTP). Dideoxynucleotides lack the 3'-OH group of dNTPs that would otherwise participate in polymerase-mediated primer extension. Thus, the 3' position has a hydrogen moiety instead of the native hydroxyl moiety. Irreversibly terminated nucleotides can be particularly useful for genotyping applications or other applications where primer extension or sequential detection along a template nucleic acid is not desired.

In some embodiments, a nucleotide that participates in forming a ternary complex can include an exogenous label. For example, an exogenously labeled nucleotide can include a reversible or irreversible terminator moiety, an exogenously labeled nucleotide can be non-incorporable, an exogenously labeled nucleotide can lack terminator moieties, an exogenously labeled nucleotide can be incorporable or an exogenously labeled nucleotide can be both incorporable and non-terminated. Exogenously labeled nucleotides can be particularly useful when used to form a stabilized ternary complex with a non-labeled polymerase. Alternatively, an exogenous label on a nucleotide can provide one partner in a fluorescence resonance energy transfer (FRET)

pair and an exogenous label on a polymerase can provide the second partner of the pair. As such, FRET detection can be used to identify a stabilized ternary complex that includes both partners. Alternatively, a nucleotide that participates in forming a ternary complex can lack exogenous labels (i.e. the nucleotide can be "non-labeled"). For example, a non-labeled nucleotide can include a reversible or irreversible terminator moiety, a non-labeled nucleotide can be non-incorporable, a non-labeled nucleotide can lack terminator moieties, a non-labeled nucleotide can be incorporable or a non-labeled nucleotide can be both incorporable and non-terminated. Non-labeled nucleotides can be useful when a label on a polymerase is used to detect a stabilized ternary complex. Non-labeled nucleotides can also be useful in an extension step of a method set forth herein. It will be understood that absence of a moiety or function for a nucleotide refers to the nucleotide having no such function or moiety. However, it will also be understood that one or more of the functions or moieties set forth herein for a nucleotide, or analog thereof, or otherwise known in the art for a nucleotide, or analog thereof, can be specifically omitted in a method or composition set forth herein.

Optionally, a nucleotide (e.g. a native nucleotide or nucleotide analog) is present in a mixture during formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 base types in a template nucleic acid. Alternatively or additionally, one or more nucleotide types that are present can be complementary to at most 4, 3, 2, or 1 base types in a template nucleic acid.

Any nucleotide modification that stabilizes a polymerase in a ternary complex may be used in the methods disclosed herein. The nucleotide may be bound permanently or transiently to a polymerase. Optionally, a nucleotide analog is fused to a polymerase, for example, via a covalent linker. Optionally, a plurality of nucleotide analogs is fused to a plurality of polymerases, wherein each nucleotide analog is fused to a different polymerase. Optionally, a nucleotide that is present in a stabilized ternary complex is not the means by which the ternary complex is stabilized. Accordingly, any of a variety of other ternary complex stabilization methods may be combined in a reaction utilizing a nucleotide analog.

In particular embodiments, the primer strand of a primer-template hybrid molecule that is present in a stabilized ternary complex is chemically unchanged by the polymerase that is present during one or more steps of a method set forth herein. For example, the primer need not be extended by formation of a new phosphodiester bond, nor shortened by nucleolytic degradation during a step for forming a stabilized ternary complex, nor during a step for detecting the stabilized ternary complex.

Any of a variety of polymerases can be used to form a stabilized ternary complex in a method set forth herein. Polymerases that may be used include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. Optionally, the naturally occurring and/or modified variations thereof have the ability to catalyze a polymerization reaction in at least one condition that is not used during formation or examination of a stabilized ternary complex. Optionally, the naturally-occurring and/or modified variations that participate in stabilized ternary complexes have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, reduced catalysis rates, catalytic inactivity etc. Mutant polymerases include, for example, polymerases wherein one or more amino acids are replaced with other amino acids, or insertions or deletions of one or more amino acids. Exemplary polymerase mutants that can be used to form a stabilized ternary complex include, for example, those set forth in U.S. patent application Ser. No. 15/866,353 (now published as US 2018/0155698 A1) or US Pat. App. Pub. No. 2017/0314072 A1, each of which is incorporated herein by reference.

Modified polymerases include polymerases that contain an exogenous label moiety (e.g., an exogenous fluorophore), which can be used to detect the polymerase. Optionally, the label moiety can be attached after the polymerase has been at least partially purified using protein isolation techniques. For example, the exogenous label moiety can be chemically linked to the polymerase using a free sulfhydryl or a free amine moiety of the polymerase. This can involve chemical linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP), phycobiliproteins (e.g. phycocyanin and phycoerythrin) or wavelength-shifted variants of GFP or phycobiliproteins. In some embodiments, an exogenous label on a polymerase can function as a member of a FRET pair. The other member of the FRET pair can be an exogenous label that is attached to a nucleotide that binds to the polymerase in a stabilized ternary complex. As such, the stabilized ternary complex can be detected or identified via FRET.

Alternatively, a polymerase that participates in a stabilized ternary complex need not be attached to an exogenous label. For example, the polymerase need not be covalently attached to an exogenous label. Instead, the polymerase can lack any label until it associates with a labeled nucleotide and/or labeled nucleic acid (e.g. labeled primer and/or labeled template).

A ternary complex that is made or used in accordance with the present disclosure may optionally include one or more exogenous label(s). The label can be attached to a component of the ternary complex (e.g. attached to the polymerase, template nucleic acid, primer and/or cognate nucleotide) prior to formation of the ternary complex. Exemplary attachments include covalent attachments or non-covalent attachments such as those set forth herein, in references cited herein or known in the art. In some embodiments, a labeled component is delivered in solution to a solid support that is attached to an unlabeled component, whereby the label is recruited to the solid support by virtue of forming a stabilized ternary complex. As such, the support-attached component can be detected or identified based on observation of the recruited label. Whether used in solution phase or on a solid support, exogenous labels can be useful for detecting a stabilized ternary complex or an individual component thereof, during an examination step. An exogenous label can remain attached to a component after the component dissociates from other components that had formed a stabilized ternary complex. Exemplary labels, methods for attaching labels and methods for using labeled components are set forth in commonly owned U.S. Pat. App. Pub. No. 2017/0022553 A1 or U.S. patent application Ser. No. 15/677,870 (published as US 2018/0044727 A1); U.S. patent application Ser. No. 15/581,383 (published as US 2018/0187245 A1); Ser. No. 15/873,343 (published as US 2018/0208983 A1); or US Pat. App. Pub. No. 2018/0208983 A1 (which claims priority to U.S. Pat. App. Ser. Nos. 62/450,397 and 62/506,759), each of which is incorporated herein by reference.

Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore moieties include, but are not limited to umbelliferone, fluorescein, isothiocyanate, rhodamine, tetramethyl rhodamine, eosin, green fluorescent protein, erythrosin, coumarin, methyl coumarin, pyrene, malachite green, stilbene, lucifer Yellow™, Cascade Blue™, Texas Red™, dansyl chloride, phycoerythrin, phycocyanin, fluorescent lanthanide complexes such as those including Europium and Terbium, Cy3, Cy5, and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

A secondary label can be used in a method of the present disclosure. A secondary label is a binding moiety that can bind specifically to a partner moiety. For example, a ligand moiety can be attached to a polymerase, nucleic acid or nucleotide to allow detection via specific affinity for labeled receptor. Exemplary pairs of binding moieties that can be used include, without limitation, antigen and immunoglobulin or active fragments thereof, such as FAbs; immunoglobulin and immunoglobulin (or active fragments, respectively); avidin and biotin, or analogs thereof having specificity for avidin; streptavidin and biotin, or analogs thereof having specificity for streptavidin; or carbohydrates and lectins.

In some embodiments, the secondary label can be a chemically modifiable moiety. In this embodiment, labels having reactive functional groups can be incorporated into a stabilized ternary complex. Subsequently, the functional group can be covalently reacted with a primary label moiety. Suitable functional groups include, but are not limited to, amino groups, carboxy groups, maleimide groups, oxo groups and thiol groups.

In alternative embodiments, a ternary complex can lack exogenous labels. For example, a ternary complex and all components participating in the ternary complex (e.g. polymerase, template nucleic acid, primer and/or cognate nucleotide) can lack one, several or all of the exogenous labels described herein or in the above-incorporated references. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. No. 2017/0022553 A1 PCT App. Ser. No. PCT/US16/68916 (published as WO 2017/117243), or U.S. Pat. App. Ser. No. 62/375,379 or Ser. No. 15/677,870 (published as US 2018/0044727 A11), each of which is incorporated herein by reference.

Generally, detection can be achieved in an examination step by methods that perceive a property that is intrinsic to a ternary complex or a label moiety attached thereto. Exemplary properties upon which detection can be based include, but are not limited to, mass, electrical conductivity, energy absorbance, fluorescence or the like. Detection of luminescence can be carried out using methods known in the art pertaining to nucleic acid arrays. A luminophore can be detected based on any of a variety of luminescence properties including, for example, emission wavelength, excitation wavelength, fluorescence resonance energy transfer (FRET) intensity, quenching, anisotropy or lifetime. Other detection techniques that can be used in a method set forth herein include, for example, mass spectrometry which can be used to perceive mass; surface plasmon resonance which can be used to perceive binding to a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques. Examples of reagents and conditions that can be used to create, manipulate and detect stabilized ternary complexes include, for example, those set forth in commonly owned U.S. Pat. App. Pub. No. 2017/0022553 A1; PCT App. Ser. No. PCT/US16/68916 (published as WO 2017/117243); or U.S. patent application Ser. No. 15/677,870 (published as 2018/0044727 A1); Ser. No. 15/851,383 (published as US 2018/0187245 A1); Ser. No. 15/873,343 (published as US 2018/0208983 A1); or US Pat. App. Pub. No. 2018/0208983 A1 (which claims priority to U.S. Pat. App. Ser. Nos. 62/450,397 and 62/506,759), each of which is incorporated herein by reference.

Particular embodiments of the methods set forth herein include a step of forming a mixture that includes several components. For example, a mixture can be formed between a primer-template nucleic acid hybrid, a polymerase and one or more nucleotide types. The components of the mixture can be delivered to a vessel in any desired order or they can be delivered simultaneously. Furthermore, some of the components can be mixed with each other to form a first mixture that is subsequently contacted with other components to form a more complex mixture. Taking as an example, a step of forming a mixture that includes a primer-template nucleic acid hybrid, a polymerase and a plurality of different nucleotide types, it will be understood that the different nucleotide types in the plurality can be contacted with each other prior to being contacted with the primer-template nucleic acid hybrid. Alternatively, two or more of the nucleotide types can be delivered separately to the primer-template hybrid and/or the polymerase. As such, a first nucleotide type can be contacted with the primer-template hybrid prior to being contacted with a second nucleotide type. Alternatively or additionally, the first nucleotide type can be contacted with the polymerase prior to being contacted with a second nucleotide type.

Some embodiments of the methods set forth herein utilize two or more distinguishable signals to distinguish stabilized ternary complexes from each other and/or to distinguish one base type in a template nucleic acid from another base type. For example, two or more luminophores can be distinguished from each other based on unique optical properties such as unique wavelength for excitation or unique wavelength of emission. In particular embodiments, a method can distinguish different stabilized ternary complexes based on differences in luminescence intensity. For example, a first ternary complex can be detected in a condition where it emits less intensity than a second ternary complex. Such intensity scaling (sometimes called 'grey scaling') can exploit any distinguishable intensity difference. Exemplary differences include a particular stabilized ternary complex having an intensity that is 10%, 25%, 33%, 50%, 66%, or 75% compared to the intensity of another stabilized ternary complex that is to be detected.

Intensity differences can be achieved using different luminophores each having a different extinction coefficient (i.e. resulting in different excitation properties) and/or different luminescence quantum yield (i.e. resulting in different emission properties). Alternatively, the same luminophore type can be used but can be present in different amounts. For example, all members of a first population of ternary complexes can be labeled with a particular luminophore, whereas a second population has only half of its members labeled with the luminophore. In this example, the second population would be expected to produce half the signal of the first population. The second population can be produced, for example, by using a mixture of labeled nucleotides and unlabeled nucleotides (in contrast to the first population containing primarily labeled nucleotides). Similarly, the second population can be produced, for example, by using a mixture of labeled polymerases and unlabeled polymerases (in contrast to the first population containing primarily labeled polymerases). In an alternative labeling scheme, a first population of ternary complexes can include polymerase molecules that have multiple labels that produce a particular luminescent signal and a second population of ternary complexes can include polymerase molecules that each have only one of the labels that produces the luminescent signal.

In some embodiments, the examination step is carried out in a way that the identity of at least one nucleotide type is imputed, for example, as set forth in commonly owned U.S. patent application Ser. No. 15/712,632 which issued as U.S. Pat. No. 9,951,385, each of which is incorporated herein by reference. For example, an examination step can include steps of (a) forming a mixture under ternary complex stabilizing conditions, wherein the mixture includes a primed template nucleic acid, a polymerase and nucleotide cognates of first, second and third base types in the template; (b) examining the mixture to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b).

Alternatively or additionally to using imputation, an examination step can use disambiguation to identify one or more nucleotide types, for example, as set forth in commonly owned U.S. patent application Ser. No. 15/712,632, which issued as U.S. Pat. No. 9,951,385, each of which is incorporated herein by reference. For example, an examination step can include steps of (a) sequentially contacting a primed template nucleic acid with at least two separate mixtures under ternary complex stabilizing conditions, wherein the at least two separate mixtures each include a polymerase and a nucleotide, whereby the sequentially contacting results in the primed template nucleic acid being contacted, under the ternary complex stabilizing conditions, with nucleotide cognates for first, second and third base base types in the template; (b) examining the at least two separate mixtures to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b).

In particular embodiments, examination can be carried out by (a) contacting a primed template nucleic acid with a polymerase and a first mixture of nucleotides under ternary complex stabilizing conditions, wherein the first mixture includes a nucleotide cognate of a first base type and a nucleotide cognate of a second base type; (b) contacting the primed template nucleic acid with a polymerase and a second mixture of nucleotides under ternary complex stabilizing conditions, wherein the second mixture includes a nucleotide cognate of the first base type and a nucleotide cognate of a third base type; (c) examining products of steps (a) and (b) for signals produced by a ternary complex that includes the primed template nucleic acid, a polymerase and a next correct nucleotide, wherein signals acquired for the product of step (a) are ambiguous for the first and second base type, and wherein signals acquired for the product of step (b) are ambiguous for the first and third base type; (d) disambiguating signals acquired in step (c) to identify a base type that binds the next correct nucleotide. Optionally, to achieve disambiguation (i) the first base type is correlated with presence of signals for the product of step (a) and presence of signals for the product of step (b), (ii) the second base type is correlated with presence of signals for the product of step (a) and absence of signals for the product of step (b), and (iii) the third base type is correlated with absence of signals for the product of step (a) and presence of signals for the product of step (b).

Also provided is a method wherein examination includes steps of (a) contacting a primed template nucleic acid with a first mixture including a polymerase, a nucleotide cognate of a first base type in the template and a nucleotide cognate a second base type in the template, wherein the contact occurs in a binding reaction that (i) stabilizes ternary complexes including the primed template nucleic acid, the polymerase and a next correct nucleotide, and (ii) prevents incorporation of the next correct nucleotide into the primer; (b) examining the binding reaction to determine whether a ternary complex formed; (c) subjecting the primed template nucleic acid to a repetition of steps (a) and (b), wherein the first mixture is replaced with a second mixture, the second mixture including a polymerase, a nucleotide cognate of the first base type in the template and a nucleotide cognate of a third base type in the template; and (d) identifying the next correct nucleotide for the primed template nucleic acid using the examination of the binding reaction, or the product thereof, wherein (i) the next correct nucleotide is identified as a cognate of the first base type if ternary complex is detected in step (b) and detected in the repetition of step (b), (ii) the next correct nucleotide is identified as a cognate of the second base type if ternary complex is detected in step (b) and undetected in the repetition of step (b), and (iii) the next correct nucleotide is identified as a cognate of the third base type if ternary complex is undetected in step (b) and detected in the repetition of step (b).

As set forth above, different activities of polymerases can be exploited in a method set forth herein. A polymerase can be useful, for example, in an extension step, examination step or both. The different activities can follow from differences in the structure (e.g. via natural activities, mutations or chemical modifications). Nevertheless, polymerase can be obtained from a variety of known sources and applied in accordance with the teachings set forth herein and recognized activities of polymerases. Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus species* 9° N (e.g., Therminator DNA polymerase from New England BioLabs Inc.; Ipswich, MA) can be used. Still other useful DNA polymerases, including the 3PDX polymerase are disclosed in U.S. Pat. No. 8,703, 461, the disclosure of which is incorporated herein by reference.

Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most genotyping and sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

Examples of reagents and conditions that can be used for a polymerase-based primer extension step include, for example, those set forth in commonly owned U.S. Pat. App. Pub. No. 2017/0022553 A1 or U.S. patent application Ser. No. 15/677,870 and its publication US 2018/0044727 A1; Ser. No. 15/581,383 and its publication US 2018/0187245 A1; or US 2018/0208983 A1 and its priority applications U.S. Ser. Nos. 62/450,397 and 62/506,759, each of which is incorporated herein by reference. Other useful reagent and conditions for polymerase-based primer extension are set forth in Bentley et al., Nature 456:53-59 (2008), WO 04/018497; WO 91/06678; WO 07/123744; U.S. Pat. No. 7,057,026; 7,329,492; 7,211,414; 7,315,019 or 7,405,281, and US Pat. App. Pub. No. 2008/0108082 A1, each of which is incorporated herein by reference.

In particular embodiments, reagents that are used during a primer extension step are removed from contact with the primer-template hybrid prior to a step of forming a stabilized ternary complex with the primer-template hybrid. For example, removal of a nucleotide mixture that was used for an extension step can be desirable when one or more types of nucleotides in the mixture would interfere with formation or detection of a ternary complex in a subsequent examination step. Similarly, it may be desirable to remove polymerases or cofactors that were used in a primer extension step so as to prevent unwanted catalytic activity during the examination step. Removal can be followed by a wash step, wherein an inert fluid is used to purge the primer-template hybrid of residual components of the extension mixture.

Wash steps can be performed between any of a variety of steps set forth herein. For example, a wash step can be useful for separating a primer-template hybrid from other reagents that were contacted with the primer-template hybrid under ternary complex stabilizing conditions. Such a wash can remove one or more reagents from interfering with examination of a mixture or from contaminating a second mixture that is to be formed on a substrate (or in a vessel) that had previously been in contact with the first mixture. For example, a primer-template nucleic acid hybrid can be contacted with a polymerase and at least one nucleotide type to form a first mixture under ternary complex stabilizing conditions, and the first mixture can be examined. Optionally, a wash can be carried out prior to examination to remove reagents that are not participating in formation of a stabilized ternary complex. Alternatively or additionally, a wash can be carried out after the examination step to remove one or more component of the first mixture from the primer-template hybrid. Then the primer-template hybrid can be contacted with a polymerase and at least one other nucleotide to form a second mixture under ternary complex stabilizing conditions, and the second mixture can be examined for ternary complex formation. As before, an optional wash can be carried out prior to the second examination to remove reagents that are not participating in formation of a stabilized ternary complex.

A method of the present disclosure can include multiple repetitions of steps set forth herein. Such repetition can provide a sequence for a template nucleic acid or a signature for the template nucleic acid. In particular embodiments, repetition produces information that can be used to determine a series of base multiplets that provide a signature for the template nucleic acid. Examination and extension steps can be repeated multiple times as can optional steps of deblocking primers, or washing away unwanted reactants or products between various steps. Accordingly, a primer-template nucleic acid hybrid can be subjected at least 2, 5, 10, 25, 50, 100 or more steps of a method set forth herein. Not all of the steps need to be repeated nor do repeated steps need to occur in the same order in each repetition. For example, next correct nucleotides at each position of a template can be identified using real time analysis (i.e. in parallel with fluidic and detection steps of a sequencing method). However, real time analysis is not necessary and instead next correct nucleotides can be identified after some or all of the fluidic and detection steps have been completed.

Accordingly, the present disclosure further provides a method of characterizing a nucleic acid. The method can include the steps of (a) contacting a primer-template nucleic acid hybrid with a polymerase and a mixture of nucleotides under conditions to produce an extended primer hybrid, wherein the mixture includes nucleotide cognates of first, second, third and fourth different base types, wherein the nucleotide cognate of the first base type has a reversible terminator, and wherein nucleotide cognates of the second, third and fourth base types are extendable; (b) contacting the extended primer hybrid with a nucleotide cognate for at least one of the different base types and a polymerase to form a stabilized ternary complex that includes the extended primer hybrid, the polymerase and a nucleotide cognate of the next base in the template; (c) detecting the stabilized ternary complex to distinguish the next base from other base types in the template; (d) determining the presence of a base multiplet in the template nucleic acid including the first base type followed by the next base; (e) repeating steps (a) through (c) using the extended primer hybrid as the primer-template nucleic acid hybrid; (f) determining the presence of a series of at least two base multiplets in the template nucleic acid; and (g) repeating steps (a) through (f), wherein the nucleotide cognate of the second base type includes a reversible terminator, and wherein nucleotide cognates of the first, third and fourth base types in the mixture are extendible, and wherein the base multiplet determined in step (c) includes the second base type followed by the next base, thereby determining the presence of two series of base multiplets in the template nucleic acid. Optionally, the method can further include (h) repeating steps (a) through (f), wherein the nucleotide cognate of the third base type includes a reversible terminator, and wherein nucleotide cognates of the first, second and fourth base types in the mixture are extendible, and wherein the base multiplet determined in step (c) includes the third base type followed by the next base, thereby determining the presence of three series of base multiplets in the template nucleic acid. As a further option, the method can include (i) repeating steps (a) through (f), wherein the nucleotide cognate of the fourth base type includes a reversible terminator, and wherein nucleotide cognates of the first, second and third base types in the mixture are extendible, and wherein the base multiplet determined in step (c) includes the fourth base type followed by the next base, thereby determining the presence of four series of base multiplets in the template nucleic acid. It will be understood by a person having ordinary skill in the art that when the steps (a) through (f) are repeated, they may be repeated using the same procedures of the previous steps (a) through (f) but with a nucleotide cognate including a reversible terminator and nucleotide cognates being extendable that differ from one or more previous iterations of the steps (a) through (f) in the same method.

The present disclosure further provides a method of characterizing a nucleic acid that includes steps of (a) contacting a primer-template nucleic acid hybrid with a polymerase and a mixture of nucleotides under conditions to produce an extended primer hybrid and to form a stabilized ternary complex that includes the extended primer hybrid, the polymerase and a nucleotide cognate of the next base in the template, wherein the mixture includes nucleotide cognates of first, second, third and fourth different base types, wherein the nucleotide cognate of the first base type comprises a reversible terminator, and wherein nucleotide cognates of the second, third and fourth base types are extendable; (b) detecting the stabilized ternary complex to distinguish the next base from other base types in the template; (c) determining the presence of a base multiplet in the template nucleic acid including the first base type followed by the next base; (d) repeating steps (a) and (b) using the extended primer hybrid as the primer-template nucleic acid hybrid; (e) determining the presence of a series of at least two base multiplets in the template nucleic acid; and (f) repeating steps (a) through (e), wherein the nucleotide cognate of the second base type has a reversible terminator, and wherein nucleotide cognates of the first, third and fourth base types in the mixture are extendible, and wherein the base multiplet determined in step (c) includes the second base type followed by the next base, thereby determining the presence of two series of base multiplets in the template nucleic acid. Optionally, the method can further include a step of (g) repeating steps (a) through (e), wherein the nucleotide cognate of the third base type has a reversible terminator, and wherein nucleotide cognates of the first, second and fourth base types in the mixture are extendible, and wherein the base multiplet determined in step (c) includes the third base type followed by the next base, thereby determining the presence of three series of base multiplets in the template nucleic acid. As a further option the method includes a step of (h) repeating steps (a) through (e), wherein the nucleotide cognate of the fourth base type has a reversible terminator, and wherein nucleotide cognates of the first, second and third base types in the mixture are extendible, and wherein the base multiplet determined in step (c) includes the fourth base type followed by the next base, thereby determining the presence of four series of base multiplets in the template nucleic acid. It will be understood by a person having ordinary skill in the art that when the steps (a) through (e) are repeated, they may be repeated using the same procedures of the previous steps (a) through (e) but with a nucleotide cognate including a reversible terminator and nucleotide cognates being extendable that differ from one or more previous iterations of the steps (a) through (e) in the same method.

Also provided is a method of characterizing a nucleic acid that includes the steps of (a) contacting a primer-template nucleic acid hybrid with a polymerase and a mixture of nucleotides under conditions to produce an extended primer hybrid, wherein the mixture includes nucleotide cognates of first, second, third and fourth different base types, wherein the nucleotide cognate of the first and second base type have a reversible terminator, and wherein nucleotide cognates of the third and fourth base types are extendable; (b) contacting the extended primer hybrid with a nucleotide cognate for at least one of the different base types and a polymerase to form a stabilized ternary complex that includes the extended primer hybrid, the polymerase and a nucleotide cognate of the next base in the template; (c) detecting the stabilized ternary complex to distinguish the next base from other base types in the template; (d) determining the presence of a base multiplet in the template nucleic acid; (e) repeating steps (a) through (c) using the extended primer hybrid as the primer-template nucleic acid hybrid; (f) determining the presence of a series of at least two base multiplets in the template nucleic acid; and (g) repeating steps (a) through (f), wherein the nucleotide cognate of the third and fourth base type includes a reversible terminator, and wherein nucleotide cognates of the first, and second base types in the mixture are extendable, thereby determining the presence of two series of base multiplets in the template nucleic acid. Optionally, the method can further include (h) repeating steps (a) through (f), wherein the nucleotide cognate of the first and third base types include a reversible terminator, and wherein nucleotide cognates of the second and fourth base types in the mixture are extendable, thereby determining the presence of three series of base multiplets in the template nucleic acid. As a further option, the method can include (i) repeating steps (a) through (f), wherein the nucleotide cognate of the second and fourth base types include a reversible terminator, and wherein nucleotide cognates of the first and third base types in the mixture are extendable, thereby determining the presence of four series of base multiplets in the template nucleic acid. It will be understood by a person having ordinary skill in the art that when the steps (a) through (f) are repeated, they may be repeated using the same procedures of the previous steps (a) through (f) but with nucleotide cognates including reversible terminators and nucleotide cognates being extendable that differ from one or more previous iterations of the steps (a) through (f) in the same method.

The present disclosure further provides a method of characterizing a nucleic acid that includes steps of (a) contacting a primer-template nucleic acid hybrid with a polymerase and a mixture of nucleotides under conditions to produce an extended primer hybrid and to form a stabilized ternary complex that includes the extended primer hybrid, the polymerase and a nucleotide cognate of the next base in the template, wherein the mixture includes nucleotide cognates of first, second, third and fourth different base types, wherein the nucleotide cognate of the first and second base types comprise a reversible terminator, and wherein nucleotide cognates of the third and fourth base types are extendable; (b) detecting the stabilized ternary complex to distinguish the next base from other base types in the template; (c) determining the presence of a base multiplet in the template nucleic acid; (d) repeating steps (a) and (b) using the extended primer hybrid as the primer-template nucleic acid hybrid; (e) determining the presence of a series of at least two base multiplets in the template nucleic acid; and (f) repeating steps (a) through (e), wherein the nucleotide cognate of the third and fourth base types have a reversible terminator, and wherein nucleotide cognates of the first and second base types in the mixture are extendable, thereby determining the presence of two series of base multiplets in the template nucleic acid. Optionally, the method can further include a step of (g) repeating steps (a) through (e), wherein the nucleotide cognate of the first and third base types have a reversible terminator, and wherein nucleotide cognates of the second and fourth base types in the mixture are extendible, thereby determining the presence of three series of base multiplets in the template nucleic acid. As a further option the method includes a step of (h) repeating steps (a) through (e), wherein the nucleotide cognate of the second and fourth base types have a reversible terminator, and wherein nucleotide cognates of the first and third base types in the mixture are extendible, thereby determining the presence of four series of base multiplets in the template nucleic acid. It will be understood by a person having ordinary skill in the art that when the steps (a) through (e) are repeated, they may be repeated using the same procedures of the previous steps (a) through (e) but with nucleotide cognates including a reversible terminators and nucleotide cognates being extendable that differ from one or more previous iterations of the steps (a) through (e) in the same method.

The present disclosure further provides a method of characterizing a nucleic acid that includes steps of (a) contacting a primer-template nucleic acid hybrid with a polymerase and a mixture of nucleotides under conditions to produce an extended primer hybrid, wherein the mixture includes nucleotide cognates of no more than three of four different base types; (b) further extending the extended primer hybrid with a nucleotide cognate of a fourth of the four different base types in the absence of the nucleotide cognates of (a), thereby producing a further extended primer hybrid; (c) forming a stabilized ternary complex that includes the further extended primer hybrid, a polymerase and a nucleotide cognate of the next base in the template; (d) detecting the stabilized ternary complex to distinguish the next base from other base types in the template; (e) determining the presence of a base multiplet in the template nucleic acid including the fourth of the four different base types followed by the next base; (f) repeating steps (a) through (d) using the further extended primer hybrid as the primer-template nucleic acid hybrid; (g) determining the presence of a series of at least two base multiplets in the template nucleic acid; and (h) repeating steps (a) through (g), wherein the nucleotide cognate of the fourth base type is replaced with a nucleotide cognate of a first base type and wherein nucleotide cognates of the first base type are not used in step (a), thereby determining the presence of two series of base multiplets in the template nucleic acid. Optionally, the method can further include (i) repeating steps (a) through (g), wherein the nucleotide cognate of the fourth base type is replaced with a nucleotide cognate of a second base type and wherein nucleotide cognates of the second base type are not used in step (a), thereby determining the presence of three series of base multiplets in the template nucleic acid. As a further option the method can include (j) repeating steps (a) through (g), wherein the nucleotide cognate of the fourth base type is replaced with a nucleotide cognate of a third base type and wherein nucleotide cognates of the third base type are not used in step (a), thereby determining the presence of four series of base multiplets in the template nucleic acid. It will be understood by a person having ordinary skill in the art that when the steps (a) through (g) are repeated, they may be repeated using the same procedures of the previous steps (a) through (g) but with a nucleotide cognate including a reversible terminator, nucleotide cognates being extendable, and unused nucleotide cognate that differ from one or more previous iterations of the steps (a) through (g) in the same method.

In particular embodiments of the above methods, several steps are repeated using a template having the same sequence. In some situations, the same template molecule is used. For example, steps can be carried out that produce an extended primer hybridized to the template; the extended primer can be removed from the template; and a new primer can be hybridized to the template for the repeated steps. The extended primer can be removed using methods known in the art for denaturing double stranded nucleic acids including for example, heat or chemical denaturants. Exemplary methods for denaturing nucleic acids are set forth in Sambrook et al., *Molecular Cloning: A Laboratory Manual,* 3rd edition, Cold Spring Harbor Laboratory, New York (2001) or in Ausubel et al., *Current Protocols in Molecular Biology,* John Wiley and Sons, Baltimore, Md. (1998), each of which is incorporated herein by reference. Generally, the template nucleic acid will be attached to a surface via covalent bonds or strong non-covalent bonds. As such, denaturing conditions can be used that are effective at separating nucleic acid strands, but gentle enough to maintain attachment of the template to the surface. The surface can then be washed or flushed to remove the extended primer while leaving the template on the surface. In some embodiments, the extended strand can be degraded, for example, via chemicals, nuclease enzymes or physical shearing. Alternatively, the template molecule is not re-used and instead a second template molecule is used in a second iteration of the method, wherein the second molecule has a template region with the same sequence as the template that was used in the first iteration of the method.

In some embodiments, a template nucleic acid can be characterized to determine the sequence of one region (at single base resolution) and to determine one or more series of base multiplets that provide a signature for a second region of the template. For example, the two regions can be contiguous such that a sequenced region is adjacent to a tail region having a signature base multiplet series. This tail signature can be located upstream or downstream of the sequenced region. The information from the two regions can be used to assist with aligning the sequence of the template with a reference sequence, for example, during a re-sequencing application.

Accordingly, the present disclosure provides a method of characterizing a nucleic acid. The method can include the steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid, wherein the mixture includes nucleotide cognates of first, second, third and fourth different base types, wherein the nucleotide cognate of the first base type has a reversible terminator, and wherein at least one of the nucleotide cognates of the second, third or fourth base types is extendable; (b) contacting the extended primer hybrid with a nucleotide cognate for at least one of the different base types and a polymerase to form a stabilized ternary complex that includes the extended primer hybrid, the polymerase and a nucleotide cognate of the next base in the template; (c) detecting the stabilized ternary complex to distinguish the next base from other base types in the template; (d) determining the presence of a base multiplet in the template nucleic acid including the first base type followed by the next base; (e) repeating steps (a) through (c) using the extended primer hybrid as the primer-template nucleic acid hybrid and (f) determining the presence of a series of at least two base multiplets in the template nucleic acid, wherein the first region of the template is 3' to the series of at least two base multiplets.

In a further embodiment, a method of characterizing a nucleic acid can include steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid and to form a stabilized ternary complex that includes the extended primer hybrid, the polymerase and a nucleotide cognate of the next base in the template, wherein the mixture includes nucleotide cognates of first, second, third and fourth different base types, wherein the nucleotide cognate of the first base type comprises a reversible terminator, and wherein at least one of the nucleotide cognates of the second, third or fourth base types is extendable; (b) detecting the stabilized ternary complex to distinguish the next base from other base types in the template; (c) determining the presence of a base multiplet in the template nucleic acid including the first base type followed by the next base; (d) repeating steps (a) and (b) using the extended primer hybrid as the primer-template nucleic acid hybrid; and I determining the presence of a series of at least two base multiplets in the template nucleic acid, wherein the first region of the template is 3' to the series of at least two base multiplets.

The present disclosure further provides a method of characterizing a nucleic acid that includes steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid, wherein the mixture includes nucleotide cognates of no more than three of four different base types; (b) further extending the extended primer hybrid with a nucleotide cognate of a fourth of the four different base types in the absence of the nucleotide cognates of (a), thereby producing a further extended primer hybrid; (c) forming a stabilized ternary complex that includes the further extended primer hybrid, a polymerase and a nucleotide cognate of the next base in the template; (d) detecting the stabilized ternary complex to distinguish the next base from other base types in the template; (e) determining the presence of a base multiplet in the template nucleic acid including the fourth of the four different base types followed by the next base; (f) repeating steps (a) through (d) using the further extended primer hybrid as the primer-template nucleic acid hybrid; and (g) determining the presence of a series of at least two base multiplets in the template nucleic acid, wherein the first region of the template is 3' to the series of at least two base multiplets.

In some embodiments, a template nucleic acid can be characterized to determine the sequence of two regions (at single base resolution) and to determine one or more series of base multiplets that provide a signature for a third region of the template that intervenes the two sequenced regions. The two regions can be analyzed as paired reads separated by a linker having a signature such as a base multiplet series signature or a length signature. Typical paired read alignment methods can be improved by aligning not only the two sequenced regions to a reference genome, but by also using the linker signature as a basis for alignment.

Accordingly, the present disclosure provides a paired read method of characterizing a template nucleic acid, wherein the template comprises a linker region that is adjacent to and between first and second regions of the template nucleic acid, wherein the method includes steps of (a) obtaining a single base resolution sequence of the first region by extending a primer along the linker region of the template nucleic acid, thereby producing an extended primer-template hybrid; (b) obtaining a signature for the linker region by (i) further extending the extended primer of the extended primer-template hybrid using a mixture of nucleotides, wherein the mixture of nucleotides comprises nucleotide cognates of first, second, third and fourth different base types, wherein the nucleotide cognate of the first base type comprises a reversible terminator, and wherein at least one of the nucleotide cognates of the second, third or fourth base types is extendable, and (ii) detecting a stabilized ternary complex, the stabilized ternary complex comprising the further extended primer-template hybrid, a polymerase and a nucleotide cognate of the next base in the template, wherein the signature comprises a base multiplet comprising the first base type followed by the next base; and (c) obtaining a single base resolution sequence of the second region by extending the primer of the further extended primer-template hybrid.

The present disclosure also provides a paired read method of characterizing a nucleic acid, wherein the template comprises a linker region that is adjacent to and between first and second regions of the template nucleic acid, wherein the method includes steps of (a) obtaining a single base resolution sequence of the first region by extending a primer along the linker region of the template nucleic acid, thereby producing an extended primer-template hybrid; (b) obtaining a signature for the linker region by (i) further extending the extended primer of the extended primer-template hybrid using a mixture of nucleotides, wherein the mixture of nucleotides comprises nucleotide cognates of no more than three of four different base types, (ii) further extending the extended primer-template hybrid of step (i) with a nucleotide cognate of a fourth of the four different base types in the absence of the nucleotide cognates of step (i), (iii) detecting a stabilized ternary complex comprising the extended primer-template hybrid of step (ii), a polymerase and a nucleotide cognate of the next base in the template, wherein the signature comprises a base multiplet comprising the fourth of the four different base types followed by the next base; and (c) obtaining a single base resolution sequence of the second region by extending the primer of the extended primer-template hybrid of step (iii).

The present disclosure also provides a paired read method of characterizing a nucleic acid, wherein the template comprises a linker region that is adjacent to and between first and second regions of the template nucleic acid, wherein the method includes steps of (a) obtaining a single base resolution sequence of the first region by extending a primer along the linker region of the template nucleic acid, thereby producing an extended primer-template hybrid; (b) obtaining a signature for the linker region by further extending the extended primer of the extended primer-template hybrid without distinguishing the types of nucleotides incorporated into the extended primer, wherein the signature comprises a count of the nucleotides in the linker region; and (c) obtaining a single base resolution sequence of the second region by extending the primer of the extended primer-template hybrid of step (b). Optionally, step (b) is carried out without the use of labeled nucleotides and labeled polymerase. Optionally, step (b) is carried out without the use of labels that distinguish different types of nucleotides that are incorporated into the extended primer-template hybrid. Optionally, step (b) is carried out without detecting the extended primer-template hybrid.

The paired read methods exemplified above allow adjacent regions of a template nucleic acid to be sequenced by extending a primer along a single strand of a nucleic acid molecule. This is in contrast to paired end methods in which a first primer is extended along a first strand of a template, followed by removal of the primer extension product from the template, followed by replication of the template to produce a second strand (i.e. the second strand being a complement of the first strand), and then followed by extension of a second primer along the second strand. Particular configurations of the paired read methods set forth herein need not include process steps to denature the product of a first sequence read from a template prior to performing a second, paired sequence read. Particular configurations of the paired read methods set forth herein need not include process steps to replicate a first strand of a template after it has been sequenced in order to produce a second strand for a second primer extension process. Particular configurations of the paired read methods set forth herein need not require primers to be extended in opposite directions along opposite strands of a template to acquire two reads, respectively.

The present disclosure also provides a method of characterizing a nucleic acid. The method can include the steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid, wherein the mixture includes nucleotide cognates of first, second, third and fourth different base types, wherein the nucleotide cognate of the first base type has a reversible terminator, and wherein at least one of the nucleotide cognates of the second, third or fourth base types is extendable; (b) contacting the extended primer hybrid with a nucleotide cognate for at least one of the different base types and a polymerase to form a stabilized ternary complex that includes the extended primer hybrid, the polymerase and a nucleotide cognate of the next base in the template; (c) detecting the stabilized ternary complex to distinguish the next base from other base types in the template; (d) determining the presence of a base multiplet in the template nucleic acid including the first base type followed by the next base; (e) repeating steps (a) through (c) using the extended primer hybrid as the primer-template nucleic acid hybrid; (f) determining the presence of a series of at least two base multiplets in the template nucleic acid, wherein the first region of the template is 3' to the series of at least two base multiplets and (g) performing polymerase extension of the extended primer in a second sequencing process, wherein the second sequencing process detects signals indicative of a sequence of the template that is 5' to the series of at least two base multiplets.

Also provided is a method of characterizing a nucleic acid that includes steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid and to form a stabilized ternary complex that includes the extended primer hybrid, the polymerase and a nucleotide cognate of the next base in the template, wherein the mixture includes nucleotide cognates of first, second, third and fourth different base types, wherein the nucleotide cognate of the first base type comprises a reversible terminator, and wherein at least one of the nucleotide cognates of the second, third or fourth base types is extendable; (b) detecting the stabilized ternary complex to distinguish the next base from other base types in the template; (c) determining the presence of a base multiplet in the template nucleic acid including the first base type followed by the next base; (d) repeating steps (a) and (b) using the extended primer hybrid as the primer-template nucleic acid hybrid; (e) determining the presence of a series of at least two base multiplets in the template nucleic acid, wherein the first region of the template is 3' to the series of at least two base multiplets; and (f) performing polymerase extension of the extended primer in a second sequencing process, wherein the second sequencing process detects signals indicative of a sequence of the template that is 5' to the series of at least two base multiplets.

In another embodiment a method of characterizing a nucleic acid can include the steps of (a) (i) performing a sequencing process that comprises polymerase extension of a primer hybridized to a template, thereby producing a primer-template nucleic acid hybrid and detecting signals indicative of a sequence of a first region of the template that is 3' to the series of at least two base multiplets, and (ii) contacting the primer-template nucleic acid hybrid with a polymerase and a mixture of nucleotides under conditions to produce an extended primer hybrid, wherein the mixture includes nucleotide cognates of no more than three of four different base types; (b) further extending the extended primer hybrid with a nucleotide cognate of a fourth of the four different base types in the absence of the nucleotide cognates of (a), thereby producing a further extended primer hybrid; (c) forming a stabilized ternary complex that includes the further extended primer hybrid, a polymerase and a nucleotide cognate of the next base in the template; (d) detecting the stabilized ternary complex to distinguish the next base from other base types in the template; (e) determining the presence of a base multiplet in the template nucleic acid including the fourth of the four different base types followed by the next base; (f) repeating steps (a) through (d) using the further extended primer hybrid as the primer-template nucleic acid hybrid; (g) determining the presence of a series of at least two base multiplets in the template nucleic acid, wherein the first region of the template is 3' to the series of at least two base multiplets; and (h) performing polymerase extension of the extended primer in a second sequencing process, wherein the second sequencing process detects signals indicative of a sequence of the template that is 5' to the series of at least two base multiplets.

A signature that is obtained using a method set forth herein can have a variety of uses, several of which are exemplified herein. Another use for a signature that is obtained using a method set forth herein is to provide a count for repeated sequences that are present in a particular template nucleic acid. For example, method set forth in US Pat. App. Pub. No. 2017/0137873 A1 (which is incorporated herein by reference) for counting single tandem repeats (STRs) or other repeated sequence elements can be modified to use methods set forth herein. Alternatively, a method or signature set forth herein can be used for purposes other than counting repeated sequence elements. For example, a method set forth herein can be used for template sequences that do not contain repeat sequence units. In such cases, a template or signature derived from a template can lack repeat sequence units, wherein the length of the missing repeat unit is at least 3, 4, 5, 10 or more nucleotides long. Alternatively or additionally, a template or signature derived from a template can be devoid of repeat units that are adjacent to each other. For example, any repeat units in a template or signature can be separated from each other by a region of non-repeated sequence that is at least 3, 4, 5, 10 or more nucleotides long.

A stabilized ternary complex, or a component that is capable of forming (i.e. participating in the formation of) a ternary complex, can be attached to a solid support. The solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The particular material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein, or ease of manipulation, or low cost of manufacture.

A particularly useful solid support is a particle such as a bead or microsphere. Populations of beads can be used for attachment of populations of stabilized ternary complexes or components capable of forming the complexes (e.g. polymerases, templates, primers or nucleotides). In some embodiments, it may be useful to use a configuration whereby each bead has a single type of stabilized ternary complex or a single type of component capable of forming the complex. For example, an individual bead can be attached to a single type of ternary complex, a single type of template allele, a single type of allele-specific primer, a single type of locus-specific primer or a single type of nucleotide. Alternatively, different types of components need not be separated on a bead-by-bead basis. As such, a single bead can bear multiple different types of ternary complexes, template nucleic acids, primers, primer-template nucleic acid hybrids and/or nucleotides. The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, bead or microsphere also can correspond to a wide variety of different forms and shapes. For example, they can be symmetrically shaped (e.g. spherical or cylindrical) or irregularly shaped (e.g. controlled pore glass). In addition, beads can be porous, thus increasing the surface area available for capture of ternary complexes or components thereof. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, a BeadChip™ Array available from Illumina, Inc. (San Diego, CA) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different types of nucleic acids are detected in parallel in a method set forth herein. Although it is also possible to serially process different types of nucleic acids using one or more steps of the methods set forth herein, parallel processing can provide cost savings, time savings and uniformity of conditions. An apparatus or method of the present disclosure can include at least 2, 10, 100, $1 \times 10^3$, $1 \times 10^4$, $1 \times 10^5$, $1 \times 10^6$, $1 \times 10^9$, or more different nucleic acids. Alternatively or additionally, an apparatus or method of the present disclosure can include at most $1 \times 10^9$, $1 \times 10^6$, $1 \times 10^5$, $1 \times 10^4$, $1 \times 10^3$, 100, 10, 2 or fewer, different nucleic acids. Accordingly, various reagents or products set forth herein as being useful in the apparatus or methods (e.g. primer-template nucleic acid hybrids or stabilized ternary complexes) can be multiplexed to have different types or species in these ranges.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays include those that are used in nucleic acid sequencing applications. For example, arrays that are used to attach amplicons of genomic fragments (often referred to as clusters) can be particularly useful. Examples of nucleic acid sequencing arrays that can be used herein include those described in Bentley et al., *Nature* 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A nucleic acid can be attached to a support in a way that provides detection at a single molecule level or at an ensemble level. For example, a plurality of different nucleic acids can be attached to a solid support in a way that an individual stabilized ternary complex that forms on one nucleic acid molecule on the support can be distinguished from all neighboring ternary complexes that form on the nucleic acid molecules of the support. As such, one or more different templates can be attached to a solid support in a format where each single molecule template is physically isolated and detected in a way that the single molecule is resolved from all other molecules on the solid support.

Alternatively, a method of the present disclosure can be carried out for one or more nucleic acid ensembles, an ensemble being a population of nucleotides having a common template sequence. Cluster methods can be used to attach one or more ensembles to a solid support. As such, an array can have a plurality of ensembles, each of the ensembles being referred to as a cluster or array feature in that format. Clusters can be formed using methods known in the art such as bridge amplification or emulsion PCR. Useful bridge amplification methods are described, for example, in U.S. Pat. Nos. 5,641,658 or 7,115,400; or U.S. Patent Pub. Nos. 2002/0055100 A1; 2004/0002090 A1; 2004/0096853 A1; 2007/0128624 A1; or 2008/0009420 A1. Emulsion PCR methods include, for example, methods described in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference in its entirety. Another useful method for amplifying nucleic acids on a surface is rolling circle amplification (RCA), for example, as described in Lizardi et al., *Nat. Genet.* 19:225-232 (1998) or US 2007/0099208 A1, each of which is incorporated herein by reference.

In particular embodiments, a stabilized ternary complex, polymerase, nucleic acid or nucleotide is attached to a flow cell surface or to a solid support in a flow cell. A flow cell allows convenient fluidic manipulation by passing solutions into and out of a fluidic chamber that contacts the support-bound, ternary complex. The flow cell also provides for detection of the fluidically manipulated components. For example, a detector can be positioned to detect signals from the solid support, such as signals from a label that is recruited to the solid support due to formation of a stabilized ternary complex. Exemplary flow cells that can be used are described, for example, in US Pat. App. Pub. No. 2010/0111768 A1, WO 05/065814 or US Pat. App. Pub. No. 2012/0270305 A1, each of which is incorporated herein by reference.

The present disclosure provides systems for detecting nucleic acids, for example, using methods set forth herein. For example, a system can be configured for reactions involving the examination of the interaction between a polymerase and a primer-template nucleic acid hybrid in the presence of nucleotides to identify one or more bases in a template nucleic acid sequence. Optionally, a system includes components and reagents for performing one or more steps set forth herein including, but not limited to, forming at least one stabilized ternary complex between a primer-template nucleic acid hybrid, polymerase and next correct nucleotide, detecting the stabilized ternary complex (es), extending the primer of each primer-template hybrid, and/or identifying a nucleotide, sequence of nucleotides, or series of base multiplets present in the template.

A system of the present disclosure can include a vessel or solid support for carrying out a nucleic acid detection method. For example, the system can include an array, flow cell, multi-well plate or other convenient apparatus. The vessel or solid support can be removable, thereby allowing it to be placed into or removed from the system. As such, a system can be configured to sequentially process a plurality of vessels or solid supports. The system can include a fluidic system having reservoirs for containing one or more of the reagents set forth herein (e.g. polymerase, primer, template nucleic acid, nucleotide(s) for ternary complex formation, nucleotides for primer extension, deblocking reagents or mixtures of such components). The fluidic system can be configured to deliver reagents to a vessel or solid support, for example, via channels or droplet transfer apparatus (e.g. electrowetting apparatus). Any of a variety of detection apparatus can be configured to detect the vessel or solid support where reagents interact. Examples include luminescence detectors, surface plasmon resonance detectors and others known in the art. Exemplary systems having fluidic and detection components that can be readily modified for use in a system herein include, but are not limited to, those set forth in US Pat. App. Pub. No. 2018/0280975 A1 and its priority application U.S. Pat. App. Ser. No. 62/481,289; U.S. Pat. Nos. 8,241,573; 7,329,860 or 8,039,817; or US Pat. App. Pub. Nos. 2009/0272914 A1 or 2012/0270305 A1, each of which is incorporated herein by reference.

Optionally, a system of the present disclosure further includes a computer processing unit (CPU) that is configured to operate system components. The same or different CPU can interact with the system to acquire, store and process signals (e.g. signals detected in a method set forth herein). In particular embodiments, a CPU can be used to determine, from the signals, the identity of the nucleotide that is present at a particular location in a template nucleic acid. In some cases, the CPU will identify a sequence of nucleotides for the template from the signals that are detected. In particular embodiments, the CPU is programmed to identify a base multiplet present in a sequence based on the identity of the nucleotide at the end of a primer that is hybridized to a template, as determined from the composition of the nucleotides in the extension mixture, and based on the identity of the next correct nucleotide, as determined from a particular binding reaction carried out using the primer-template hybrid.

A useful CPU can include one or more of a personal computer system, server computer system, thin client, thick client, hand-held or laptop device, multiprocessor system, microprocessor-based system, set top box, programmable consumer electronic, network PC, minicomputer system, mainframe computer system, smart phone, and distributed cloud computing environments that include any of the above systems or devices, and the like. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks set forth herein.

The components of a CPU may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g. a mouse), a display, such as a graphical user interface (GUI), or other device that facilitates interaction of a use with the nucleic acid detection system. Similarly, the CPU can communicate with other devices (e.g., via network card, modem, etc.). Such communication can occur via I/O interfaces. Still yet, a CPU of a system herein may communicate with one or more networks such as a local area network (LAN), a general wide area network (WAN), and/or a public network (e.g., the Internet) via a suitable network adapter.

This disclosure further provides kits for characterizing nucleic acids. A kit can include reagents for carrying out one or more of the methods set forth herein. For example, a kit can include reagents for producing a stabilized ternary complex when mixed with one or more primer-template nucleic acid hybrid. More specifically, a kit can include one or more of the mixtures of nucleotides used in a method set forth herein, including for example, the methods set forth in the Examples section below. In addition to the nucleotide mixtures the kit can include a polymerase that is capable of forming a stabilized ternary complex and/or a polymerase used for an extension step. The nucleotides, polymerase or both can include an exogenous label, for example, as set forth herein in the context of various methods.

Accordingly, any of the components or articles used in performing the methods set forth herein can be usefully packaged into a kit. For example, the kits can be packed to include some, many or all of the components or articles used in performing the methods set forth herein. Exemplary components include, for example, labeled nucleotides (e.g. extendible labeled nucleotides), polymerases (labeled or unlabeled), nucleotides having terminator moieties (e.g. unlabeled, reversibly terminated nucleotides), deblocking reagents and the like as set forth herein and in references cited herein. Any of such reagents can include, for example, some, many or all of the buffers, components and/or articles used for performing one or more of the subsequent steps for analysis of a primer-template nucleic acid hybrid. A kit need not include a primer or template nucleic acid. Rather, a user of the kit can provide a primer-template nucleic acid hybrid which is to be combined with components of the kit.

One or more ancillary reagents also can be included in a kit. Such ancillary reagents can include any of the reagents exemplified above and/or other types of reagents useful in performing the methods set forth herein. Instructions can further be included in a kit. The instructions can include, for example, procedures for making any components or articles used in the methods set forth herein, performing one or more steps of any embodiment of the methods set forth herein and/or instructions for performing any of the subsequent analysis steps employing a primer-template nucleic acid hybrid.

In particular embodiments, a kit includes a cartridge having reservoirs to contain the reagents and further having fluidic components for transferring reagents from the reservoirs to a detection instrument. For example, the fluidic components can be configured to transfer reagents to a flow cell where stabilized ternary complexes are detected. An exemplary fluidic cartridge that can be included in a kit (or system) of the present disclosure is described in US Pat. App. Pub. No. 2018/0280975 and its priority application U.S. Pat. App. Ser. No. 62/481,289, each of which is incorporated herein by reference.

ADDITIONAL EMBODIMENTS

1. A method of characterizing a nucleic acid, comprising
    (a) contacting a primer-template nucleic acid hybrid with a polymerase and a mixture of nucleotides under conditions to produce an extended primer hybrid,
    wherein the mixture comprises nucleotide cognates of first, second, third and fourth different base types, wherein the nucleotide cognate of the first base type comprises a reversible terminator, and wherein at least one of the nucleotide cognates of the second, third or fourth base types is extendable;
    (b) contacting the extended primer hybrid with a nucleotide cognate for at least one of the different base types and a polymerase to form a stabilized ternary complex comprising the extended primer hybrid, the polymerase and a nucleotide cognate of the next base in the template;
    (c) detecting the stabilized ternary complex to distinguish the next base from other base types in the template; and
    (d) determining the presence of a base multiplet in the template nucleic acid comprising the first base type followed by the next base.
2. The method of embodiment 1, further comprising
    (e) repeating steps (a) through (c) using the extended primer hybrid as the primer-template nucleic acid hybrid and
    (f) determining the presence of a series of at least two base multiplets in the template nucleic acid.
3. The method of embodiment 2, wherein the nucleotide cognates of the second, third and fourth base types are extendable in step (a).
4. The method of embodiment 3, further comprising
    (g) repeating steps (a) through (f), wherein the nucleotide cognate of the second base type comprises a reversible terminator, and wherein nucleotide cognates of the first, third and fourth base types in the mixture are extendible, and wherein the base multiplet determined in step (c) comprises the second base type followed by the next base,
    thereby determining the presence of two series of base multiplets in the template nucleic acid.
5. The method of one of embodiments 3 to 4, further comprising
    (h) repeating steps (a) through (f), wherein the nucleotide cognate of the third base type comprises a reversible terminator, and wherein nucleotide cognates of the first, second and fourth base types in the mixture are extendible, and wherein the base multiplet determined in step (c) comprises the third base type followed by the next base; and
    (i) repeating steps (a) through (f), wherein the nucleotide cognate of the fourth base type comprises a reversible terminator, and wherein nucleotide cognates of the first, second and third base types in the mixture are extendible, and wherein the base multiplet determined in step (c) comprises the fourth base type followed by the next base,
    thereby determining the presence of four series of base multiplets in the template nucleic acid.
6. The method of embodiment 5, further comprising a computer assisted process of aligning the four series of base multiplets to determine a sequence of the nucleic acid.
7. The method of embodiment 2, wherein the nucleotide cognates of the first and second base types comprise a reversible terminator, and wherein the nucleotide cognates of the third and fourth base types are extendable in step (a).
8. The method of embodiment 7, further comprising
    (g) repeating steps (a) through (f), wherein the nucleotide cognate of the third and fourth base types comprise a reversible terminator, and wherein nucleotide cognates of the first and second base types in the mixture are extendible.
9. The method of embodiment 8, further comprising
    (h) repeating steps (a) through (f), wherein the nucleotide cognates of the first and third base types comprise a reversible terminator, and wherein nucleotide cognates of the second and fourth base types in the mixture are extendible.
10. The method of any one of embodiments 2 to 9, wherein steps (a) through (f) are repeated using the template nucleic acid after removing the extended primer from the extended primer hybrid and then hybridizing a second primer to the template.
11. The method of any one of embodiments 2 to 9, wherein steps (a) through (f) are repeated using a second template nucleic acid molecule having the same sequence as the template nucleic acid used in step (a).
12. The method of embodiment 2, wherein the primer-template nucleic acid hybrid of step (a) is the product of polymerase extension during a sequencing process, wherein the sequencing process detects signals indicative of a sequence of the template that is 3' to the series of at least two base multiplets.
13. The method of embodiment 12, further comprising a computer assisted process of aligning the sequence of the template to a region of a reference genome, wherein the aligning is carried out by aligning the region of the reference genome to the sequence of the template that is 3' to the series of at least two base multiplets.
14. The method of embodiment 13, further comprising (g) performing polymerase extension of the extended primer in a second sequencing process, wherein the second sequencing process detects signals indicative of a sequence of the template that is 5' to the series of at least two base multiplets.
15. The method of embodiment 14, further comprising the computer assisted process of aligning the sequence of the template to a region of the reference genome, wherein the aligning is carried out by aligning the region of the reference genome to the sequence of the template that is 3' to the series of at least two base multiplets, the series of at least two base multiplets, and the sequence of the template that is 5' to the series of at least two base multiplets.
16. The method of any one of embodiments 1 to 15, wherein the nucleotide cognates of first, second, third and fourth different base types comprise exogenous labels that are detected in step (c).
17. The method of any one of embodiments 1 through 15, wherein the nucleotide cognates of first, second, third and fourth different base types do not comprise exogenous labels that are detected in step (c).

18. The method of any one of embodiments 1 through 17, wherein the polymerase comprises an exogenous label that is detected in step (c).
19. The method of any one of embodiments 1 through 18, wherein step (b) is performed after removing the mixture from contact with the extended primer hybrid.
20. A method of characterizing a nucleic acid, comprising
    (a) contacting a primer-template nucleic acid hybrid with a polymerase and a mixture of nucleotides under conditions to produce an extended primer hybrid and to form a stabilized ternary complex comprising the extended primer hybrid, the polymerase and a nucleotide cognate of the next base in the template,
    wherein the mixture comprises nucleotide cognates of first, second, third and fourth different base types, wherein the nucleotide cognate of the first base type comprises a reversible terminator, and wherein at least one of the nucleotide cognates of the second, third or fourth base types is extendable;
    (b) detecting the stabilized ternary complex to distinguish the next base from other base types in the template; and
    (c) determining the presence of a base multiplet in the template nucleic acid comprising the first base type followed by the next base.
21. The method of embodiment 20, further comprising
    (d) repeating steps (a) and (b) using the extended primer hybrid as the primer-template nucleic acid hybrid; and
    (e) determining the presence of a series of at least two base multiplets in the template nucleic acid.
22. The method of embodiment 21, wherein the nucleotide cognates of the second, third and fourth base types are extendable in step (a).
23. The method of embodiment 22, further comprising
    (f) repeating steps (a) through (e), wherein the nucleotide cognate of the second base type comprises a reversible terminator, and wherein nucleotide cognates of the first, third and fourth base types in the mixture are extendible, and wherein the base multiplet determined in step (c) comprises the second base type followed by the next base,
    thereby determining the presence of two series of base multiplets in the template nucleic acid.
24. The method of embodiment 23, further comprising
    (g) repeating steps (a) through (e), wherein the nucleotide cognate of the third base type comprises a reversible terminator, and wherein nucleotide cognates of the first, second and fourth base types in the mixture are extendible, and wherein the base multiplet determined in step (c) comprises the third base type followed by the next base; and
    (h) repeating steps (a) through (e), wherein the nucleotide cognate of the fourth base type comprises a reversible terminator, and wherein nucleotide cognates of the first, second and third base types in the mixture are extendible, and wherein the base multiplet determined in step (c) comprises the fourth base type followed by the next base,
    thereby determining the presence of four series of base multiplets in the template nucleic acid.
25. The method of embodiment 24, further comprising a computer assisted process of aligning the four series of base multiplets to determine a sequence of the nucleic acid.
26. The method of embodiment 21, wherein the nucleotide cognates of the first and second base types comprise a reversible terminator, and wherein the nucleotide cognates of the third and fourth base types are extendable in step (a).
27. The method of embodiment 26, further comprising
    (f) repeating steps (a) through (e), wherein the nucleotide cognate of the third and fourth base types comprise a reversible terminator, and wherein nucleotide cognates of the first and second base types in the mixture are extendible.
28. The method of embodiment 27, further comprising
    (g) repeating steps (a) through (e), wherein the nucleotide cognates of the first and third base types comprise a reversible terminator, and wherein nucleotide cognates of the second and fourth base types in the mixture are extendible.
29. The method of any one of embodiments 21 to 28, wherein steps (a) through (e) are repeated using the template nucleic acid after removing the extended primer from the extended primer hybrid and then hybridizing a second primer to the template.
30. The method of any one of embodiments 21 to 28, wherein steps (a) through (e) are repeated using a second template nucleic acid molecule having the same sequence as the template nucleic acid used in step (a).
31. The method of embodiment 21, wherein the primer-template nucleic acid hybrid of step (a) is the product of polymerase extension during a sequencing process, wherein the sequencing process detects signals indicative of a sequence of the template that is 3' to the series of at least two base multiplets.
32. The method of embodiment 31, further comprising the computer assisted process of aligning the sequence of the template to a region of the reference genome, wherein the aligning is carried out by aligning the region of the reference genome to the sequence of the template that is 3' to the series of at least two base multiplets.
33. The method of embodiment 32, further comprising (f) performing polymerase extension of the extended primer in a second sequencing process, wherein the second sequencing process detects signals indicative of a sequence of the template that is 5' to the series of at least two base multiplets.
34. The method of embodiment 33, further comprising the computer assisted process of aligning the sequence of the template to a region of the reference genome, wherein the aligning is carried out by aligning the region of the reference genome to the sequence of the template that is 3' to the series of at least two base multiplets, the series of at least two base multiplets, and the sequence of the template that is 5' to the series of at least two base multiplets.
35. The method of any one of embodiments 20 through 34, wherein the nucleotide cognates of first, second, third and fourth different base types comprise exogenous labels that are detected in step (b).
36. The method of any one of embodiments 20 through 34, wherein the nucleotide cognates of first, second, third and fourth different base types do not comprise exogenous labels that are detected in step (b).
37. The method of any one of embodiments 20 through 36, wherein the polymerase comprises an exogenous label that is detected in step (b).

38. A method of characterizing a nucleic acid, comprising
   (a) contacting a primer-template nucleic acid hybrid with a polymerase and a mixture of nucleotides under conditions to produce an extended primer hybrid, wherein the mixture comprises nucleotide cognates of no more than three of four different base types;
   (b) further extending the extended primer hybrid with a nucleotide cognate of a fourth of the four different base types in the absence of the nucleotide cognates of (a), thereby producing a further extended primer hybrid;
   (c) forming a stabilized ternary complex comprising the further extended primer hybrid, a polymerase and a nucleotide cognate of the next base in the template;
   (d) detecting the stabilized ternary complex to distinguish the next base from other base types in the template; and
   (e) determining the presence of a base multiplet in the template nucleic acid comprising the fourth of the four different base types followed by the next base.
39. The method of embodiment 38, further comprising
   (f) repeating steps (a) through (d) using the further extended primer hybrid as the primer-template nucleic acid hybrid and
   (g) determining the presence of a series of at least two base multiplets in the template nucleic acid.
40. The method of embodiment 39, further comprising
   (h) repeating steps (a) through (g), wherein the nucleotide cognate of the fourth base type is replaced with a nucleotide cognate of a first base type and wherein nucleotide cognates of the first base type are not used in step (a) and the three other nucleotide cognates are used,
   thereby determining the presence of two series of base multiplets in the template nucleic acid.
41. The method of embodiment 40, further comprising
   (i) repeating steps (a) through (g), wherein the nucleotide cognate of the first base type is replaced with a nucleotide cognate of a second base type and wherein nucleotide cognates of the second base type are not used in step (a) and the three other nucleotide cognates are used; and
   (j) repeating steps (a) through (g), wherein the nucleotide cognate of the second base type is replaced with a nucleotide cognate of a third base type and wherein nucleotide cognates of the third base type are not used in step (a) and the three other nucleotide cognates are used,
   thereby determining the presence of four series of base multiplets in the template nucleic acid.
42. The method of embodiment 41, further comprising the computer assisted process of aligning the four series of base multiplets to determine a sequence of the nucleic acid.
43. The method of any one of embodiments 41 to 42, wherein steps (a) through (g) are repeated using a primer-template nucleic acid hybrid produced removing the extended primer from the extended primer hybrid and hybridizing another primer to the template.
44. The method of any one of embodiments 41 to 42, wherein steps (a) through (g) are repeated using a primer-template nucleic acid hybrid molecule having the same sequence as the primer-template nucleic acid hybrid used in step (a).
45. The method of embodiment 39, wherein the primer-template nucleic acid hybrid of step (a) is the product of polymerase extension during a sequencing process, wherein the sequencing process detects signals indicative of a sequence of the template that is 3' to the series of at least two base multiplets.
46. The method of embodiment 45, further comprising the computer assisted process of aligning the sequence of the template to a region of the reference genome, wherein the aligning is carried out by aligning the region of the reference genome to the sequence of the template that is 3' to the series of at least two base multiplets.
47. The method of any one of embodiments 1 to 46, wherein the sequencing process comprises detecting stabilized ternary complexes at each position of the template, detecting labeled nucleotides incorporated into a primer at each position of the template, detecting labeled oligonucleotides ligated to the primer, detecting pyrophosphate produced due to nucleotide incorporated into a primer at each position of the template, or detecting proton produced due to nucleotide incorporated into a primer at each position of the template.
48. The method of embodiment 47, further comprising (h) performing polymerase extension of the extended primer in a second sequencing process, wherein the second sequencing process detects signals indicative of a sequence of the template that is 5' to the series of at least two base multiplets.
49. The method of embodiment 48, further comprising the computer assisted process of aligning the sequence of the template to a region of the reference genome, wherein the aligning is carried out by aligning the region of the reference genome to the sequence of the template that is 3' to the series of at least two base multiplets, the series of at least two base multiplets, and the sequence of the template that is 5' to the series of at least two base multiplets.
50. The method of any one of embodiments 21 through 49, wherein the nucleotide cognates of first, second, third and fourth different base types comprise exogenous labels that are detected in step (d).
51. The method of any one of embodiments 21 through 49, wherein the nucleotide cognates of first, second, third and fourth different base types do not comprise exogenous labels that are detected in step (d).
52. The method of any one of embodiments 21 through 51, wherein the polymerase comprises an exogenous label that is detected in step (d).
53. The method of any one of embodiments 36 through 52, wherein step (b) is performed after removing the mixture from contact with the extended primer hybrid.
54. The method of any one of embodiments 36 through 53, wherein step (c) is performed after removing the nucleotide cognate of the fourth of the four different base types.
55. A method of characterizing a template nucleic acid, wherein the template comprises a linker region that is adjacent to and between first and second regions of the template nucleic acid, comprising steps of
   (a) obtaining a single base resolution sequence of the first region by extending a primer along the first region of the template nucleic acid, thereby producing an extended primer-template hybrid;
   (b) obtaining a signature for the linker region by
      (i) further extending the extended primer of the extended primer-template hybrid using a mixture of nucleotides, wherein the mixture of nucleotides comprises nucleotide cognates of first, second, third and fourth different base types, wherein the nucleotide cognate of the first base type comprises a reversible terminator, and wherein at least one of the nucleotide cognates of the second, third or fourth base types is extendable, and
  (ii) detecting a stabilized ternary complex, the stabilized ternary complex comprising the further extended primer-template hybrid, a polymerase and a nucleotide cognate of the next base in the template, wherein the signature comprises a base multiplet comprising the first base type followed by the next base; and
(c) obtaining a single base resolution sequence of the second region by extending the further extended primer of the further extended primer-template hybrid.
56. A method of characterizing a nucleic acid, wherein the template comprises a linker region that is adjacent to and between first and second regions of the template nucleic acid, comprising steps of
(a) obtaining a single base resolution sequence of the first region by extending a primer along the first region of the template nucleic acid, thereby producing an extended primer-template hybrid;
(b) obtaining a signature for the linker region by
  (i) further extending the extended primer of the extended primer-template hybrid using a mixture of nucleotides, wherein the mixture of nucleotides comprises nucleotide cognates of no more than three of four different base types,
  (ii) further extending the extended primer-template hybrid of step (i) with a nucleotide cognate of a fourth of the four different base types in the absence of the nucleotide cognates of step (i),
  (iii) detecting a stabilized ternary complex comprising the further extended primer-template hybrid of step (ii), a polymerase and a nucleotide cognate of the next base in the template, wherein the signature comprises a base multiplet comprising the fourth of the four different base types followed by the next base; and
(c) obtaining a single base resolution sequence of the second region by extending the further extended primer of the further extended primer-template hybrid of step (iii).
57. A method of characterizing a nucleic acid, wherein the template comprises a linker region that is adjacent to and between first and second regions of the template nucleic acid, comprising steps of
(a) obtaining a single base resolution sequence of the first region by extending a primer along the first region of the template nucleic acid, thereby producing an extended primer-template hybrid;
(b) obtaining a signature for the linker region by further extending the extended primer of the extended primer-template hybrid without distinguishing the types of nucleotides incorporated into the extended primer, wherein the signature comprises a count of the nucleotides in the linker region; and
(c) obtaining a single base resolution sequence of the second region by extending the primer of the extended primer-template hybrid of step (b).
58. The method of embodiment 57, wherein step (b) is carried out without the use of labeled nucleotides and labeled polymerase.
59. The method of embodiment 57, wherein step (b) is carried out without the use of labels that distinguish different types of nucleotides that are incorporated into the extended primer-template hybrid.
60. The method of embodiment 57, wherein step (b) is carried out without detecting the extended primer-template hybrid.

Example 1

Mixed Extension Using 3 Extendible Nucleotides and 1 Reversibly Terminated Nucleotide This example describes a method for determining four dinucleotide series for a template nucleic acid. One or more dinucleotide series can be used as a signature for the template. The four dinucleotide series can be aligned to determine the sequence of the template at single nucleotide resolution.

A template nucleic acid is attached to the inner surface of an optically transparent flow cell. A primer is hybridized to the template nucleic acid. The primer includes a 3' reversible terminator moiety, the terminator moiety having been introduced, for example, via chemical synthesis or via polymerase catalyzed extension using a reversibly terminated nucleotide. Extension of the primer, following deblocking of the reversible terminator moiety, is expected to add the following sequence of nucleotides to the primer:

(SEQ ID NO: 3)
5'-TAGCCATCTGACTAACCTACTGTTT-3'

The primed nucleic acid template is subjected to a Sequencing By Binding™ procedure as follows:
  (1) Optional examination of first nucleotide—an examination solution consisting of polymerase and four labeled nucleotides (dATP, dCTP, dGTP and dTTP) is introduced to the flow cell under conditions to form a stabilized ternary complex consisting of the primer-template hybrid, polymerase and next correct nucleotide. The ternary complex is detected under conditions to distinguish signals produced by each of the nucleotides when participating in ternary complexes. The next correct nucleotide produces a signal indicative of dTTP binding and, thus the first nucleotide for the extension product is identified as T.
  (2) Deblocking—the examination solution is removed from the flow cell and replaced with a deblocking reagent that removes the reversible terminator moiety from the primer, thereby rendering the primer extendable.
  (3) $1^{st}$ run extension—the deblocking solution is removed from the flow cell and replaced with an extension mixture that includes a polymerase and 3 extendable nucleotides (dATP, dCTP and dGTP) and a reversibly terminated nucleotide ($_{rt}$dTTP). The nucleotides are not labeled. The flow cell is incubated in conditions that allow primer extension until the next $_{rt}$dTTP is incorporated.
  (4) $1^{st}$ run examination—the examination solution is introduced to the flow cell under conditions to form a stabilized ternary complex and the ternary complex is detected to determine the identity of the nucleotide that follows the $_{rt}$dTTP. A dinucleotide is identified as TN, where T is the incorporated $_{rt}$dTTP and N is any one of A, C, T or G. In one configuration, the extension and examination steps are fluidically separated by replacing the extension mixture with the examination solution.

Alternatively, the extension mixture and examination solution can be present together in the flow cell (e.g. via co-delivery or additive delivery, such that steps (3) and (4) are effectively combined).

(5) Repeat steps (2) through (4) until signal to noise decay indicates the 1$^{st}$ Run is complete—the result is a series of dinucleotides [TA][TC][TG][TA][TA][TG][TT][TT] where the number and types of nucleotides between each dinucleotide is apparently ambiguous.

(6) Strip 1$^{st}$ Run extension product—the flow cell is treated with a chemical denaturant and/or heat to remove the extended primer from the template nucleic acid.

(7) Re-apply primer—The flow cell is incubated with a primer having the same sequence and reversible terminator as was used previously, thereby re-forming the primer-template nucleic acid hybrid.

(8) Optionally the 1$^{st}$ nucleotide is again detected as described for step (1).

(9) Deblocking is carried out as in step (2).

(10) 2$^{nd}$ run extension—the deblocking solution is removed from the flow cell and replaced with an extension mixture that includes a polymerase and 3 extendable nucleotides (dCTP, dGTP and dTTP) and a reversibly terminated nucleotide ($_{rt}$dATP). The nucleotides are not labeled. The flow cell is incubated in conditions that allow primer extension until the next $_{rt}$dATP is incorporated.

(11) 2$^{nd}$ run examination—the examination solution is introduced to the flow cell under conditions to form a stabilized ternary complex and the ternary complex is detected to determine the identity of the nucleotide that follows the $_{rt}$dATP. A dinucleotide is identified as AN, where A is the incorporated $_{rt}$dTTP and N is any one of A, C, T or G. Again, extension and examination can be fluidically separated or coincident.

(12) Repeat steps (9) through (11) until signal to noise decay indicates the 2$^{nd}$ Run is complete—the result is a series of dinucleotides [AG][AT][AC][AA][AC][AC] where the number and types of nucleotides between each dinucleotide is apparently ambiguous.

(13) Repeat steps (6) through (12) replacing the 2$^{nd}$ Run extension mixture with a 3$^{rd}$ Run extension mixture that includes a polymerase, 3 extendable nucleotides (dGTP, dTTP and dATP) and a reversibly terminated nucleotide ($_{rt}$dCTP). The result is a series of dinucleotides [CC][CA][CT][CT][CC][CT][CT] where the number and types of nucleotides between each dinucleotide is apparently ambiguous.

(14) Repeat steps (6) through (12) replacing the 2$^{nd}$ Run extension mixture with a 4$^{th}$ Run extension mixture that includes a polymerase, 3 extendable nucleotides (dTTP, dATP and dCTP) and a reversibly terminated nucleotide ($_{rt}$dGTP). The result is a series of dinucleotides [GC][GA][GT] where the number and types of nucleotides between each dinucleotide is apparently ambiguous.

The extension mixtures used for each of the 4 runs and dinucleotide series determined from the runs are shown in Table 1.

TABLE 1

| Run | Extension Mix | Dinucleotide Series |
|---|---|---|
| 1 | A/C/G/$_{rt}$T | T [TA][TC][TG][TA][TA][TG][TT][TT] |
| 2 | C/G/T/$_{rt}$A | T [AG][AT][AC][AA][AC][AC] |
| 3 | G/T/A/$_{rt}$C | T [CC][CA][CT][CT][CC][CT][CT] |
| 4 | T/A/C/$_{rt}$G | T [GC][GA][GT] |

One or more of the dinucleotide series shown in Table 1 can be used as a signature for the template. In cases where the complexity of background sequences in a sample is expected to be low, a relatively short dinucleotide series can suffice as a unique signature for identifying the template in the sample. The longer the series the more distinguishing power it can have in backgrounds of ever increasing sequence complexity.

Moreover, the four dinucleotide series can be combined to determine the sequence of the template at single nucleotide resolution. Conceptually, the sequence can be determined by aligning the dinucleotides. The alignment can start with the first nucleotide, T, as determined from the first examination step (or as otherwise known). The second nucleotide in the sequence is understood to follow T and can thus be determined from the run in which extension terminated at $_{rt}$T (i.e. the 1$^{st}$ Run). In this case the second nucleotide is A. The third nucleotide in the sequence is understood to follow A and can thus be determined from the run in which extension terminated at $_{rt}$A (i.e. the 2$^{nd}$ Run). The process can continue in this way, and as visually presented in the alignment of Table 2.

TABLE 2

```
T A      T C       T A       A C
 A G      C T       A A       C T
  G C      T G       A C       T G
   C C      G A       C C       G T
    C A      A C       C T       T T
     A T      C T       T A       T T

T A G C C A T C T G A C T A A C C T A C T G T T T
(SEQ ID NO: 3)
```

Example 2

Mixed Extension Using Only 3 Nucleotides

A primer-template nucleic acid hybrid is attached to the inner surface of an optically transparent flow cell as set forth in Example 1. The primer-template hybrid has the same sequence as indicated in Example 1 and the primer optionally has a 3' reversible terminator moiety at its 3' end.

The primed nucleic acid template is subjected to a Sequencing By Binding™ procedure as follows:

(1) Optional examination of first nucleotide—an examination solution consisting of polymerase and four labeled nucleotides (dATP, dCTP, dGTP and dTTP) is introduced to the flow cell under conditions to form a stabilized ternary complex consisting of the primer-template hybrid, polymerase and next correct nucleotide. The ternary complex is stabilized via (a) a reversible terminator moiety on the 3' end of the primer, (b) a polymerase inhibitor such as a non-catalytic metal, (c) absence of a catalytic metal, and/or (d) a polymerase mutant that is inhibited in its ability to extend a primer. The ternary complex is detected under conditions to distinguish signals produced by each of the nucleotides when participating in ternary complexes. The next correct nucleotide produces a signal indicative of dTTP binding and, thus the first nucleotide for the extension product is identified as T.

(2) Activation—the examination solution is removed from the flow cell. The primer-template hybrid is activated via (a) deblocking of a reversible terminator on the primer, (b) removal of a polymerase inhibitor, (c) addition of a catalytic metal ion, and/or (d) addition of a catalytically active polymerase. The primer is thus prepared for extension.

(3) $1^{st}$ run single nucleotide extension—a single nucleotide extension solution that includes unlabeled dTTP (or $_{rt}$dTTP) and a polymerase is added to the flow cell. The flow cell is incubated in conditions that allow the primer to be extended by adding the previously omitted dTTP (or $_{rt}$dTTP). Activation is then carried out as in step (2).

(4) $1^{st}$ run mixed extension—the single nucleotide extension mixture is removed and replaced with an extension mixture that includes a polymerase and 3 extendable nucleotides (dATP, dCTP and dGTP). The nucleotides are not labeled. The flow cell is incubated in conditions that allow primer extension until the next correct nucleotide is the missing dTTP.

(5) $1^{st}$ run examination—the examination solution is introduced to the flow cell under conditions to form a stabilized ternary complex and the ternary complex is detected to determine the identity of the nucleotide that follows the dTTP. A dinucleotide is identified as TN, where N is the nucleotide that follows the T.

(6) Repeat steps (2) through (5) until signal to noise decay indicates the $1^{st}$ Run is complete—the result is a series of dinucleotides [TA][TC][TG][TA][TA][TG][TT][TT] where the number and types of nucleotides between each dinucleotide is apparently ambiguous.

(7) Strip $1^{st}$ Run extension product—the flow cell is treated with a chemical denaturant and/or heat to remove the extended primer from the template nucleic acid.

(8) Re-apply primer—The flow cell is incubated with a primer having the same sequence as was used previously, thereby re-forming the primer-template nucleic acid hybrid.

(9) Optionally the $1^{st}$ nucleotide is again detected as described for step (1).

(10) Activation is carried out as in step (2).

(11) $2^{nd}$ run mixed extension—an extension mixture that includes a polymerase and 3 extendable nucleotides (CTP, GTP and TTP) is added to the flow cell. The nucleotides are not labeled. The flow cell is incubated in conditions that allow primer extension until the next correct nucleotide is the missing ATP.

(12) $2^{nd}$ run single nucleotide extension—the extension mixture is removed and replaced with a single nucleotide extension solution that includes unlabeled ATP (or $_{rt}$ATP) and a polymerase. The flow cell is incubated in conditions that allow the primer to be extended by adding the previously omitted ATP (or $_{rt}$ATP).

(13) $2^{nd}$ run examination—the examination solution is introduced to the flow cell under conditions to form a stabilized ternary complex and the ternary complex is detected to determine the identity of the nucleotide that follows the ATP. A dinucleotide is identified as AN, where N is any one of A, C, T or G.

(14) Repeat steps (10) through (13) until signal to noise decay indicates the $2^{nd}$ Run is complete—the result is a series of dinucleotides [AG][AT][AC][AA][AC][AC] where the number and types of nucleotides between each dinucleotide is apparently ambiguous.

(15) Repeat steps (7) through (14) replacing the $2^{nd}$ Run extension mixture with a $3^{rd}$ Run extension mixture that includes a polymerase and 3 extendable nucleotides (GTP, TTP and ATP). The result is a series of dinucleotides [CC][CA][CT][CT][CC][CT][CT] where the number and types of nucleotides between each dinucleotide is apparently ambiguous.

(16) Repeat steps (7) through (14) replacing the $2^{nd}$ Run extension mixture with a $4^{th}$ Run extension mixture that includes a polymerase and 3 extendable nucleotides (dTTP, dATP and dCTP). The result is a series of dinucleotides [GC][GA][GT] where the number and types of nucleotides between each dinucleotide is apparently ambiguous.

The extension mixtures used for each of the 4 runs and dinucleotide series determined from the runs are shown in Table 3.

TABLE 3

| Run | Extension Mix | Dinucleotide Series |
| --- | --- | --- |
| 1 | A/C/G | T [TA][TC][TG][TA][TA][TG][TT][TT] |
| 2 | C/G/T | T [AG][AT][AC][AA][AC][AC] |
| 3 | G/T/A | T [CC][CA][CT][CT][CC][CT][CT] |
| 4 | T/A/C | T [GC][GA][GT] |

One or more of the dinucleotide series shown in Table 3 can be used as a signature for the template. Moreover, the four dinucleotide series can be combined to determine the sequence of the template at single nucleotide resolution using an alignment method similar to that set forth above in Example 1.

Example 3

Sequencing Using Single Nucleotide Resolution Methods Coupled with Dinucleotide Signature Determination This example describes a method for identifying a template sequence by determining the sequence for a first region of the template at single nucleotide resolution and determining a signature dinucleotide series for an adjacent tail region of the template. The signature tail region can assist with aligning the template with a reference genome and can provide long range structural information regarding the genome.

A plurality of template nucleic acids is attached to the inner surface of an optically transparent flow cell. Primers are hybridized to the template nucleic acids. The primers include a 3' reversible terminator moiety (e.g. the terminator moiety having been introduced via chemical synthesis or via polymerase catalyzed extension using a reversibly terminated nucleotide).

The primed nucleic acid templates are subjected to a Sequencing By Binding™ procedure as follows:
  (A) Single nucleotide resolution SBB™ procedure for a first region of a template—examination, deblocking, and single nucleotide extension are carried out as follows:

(1) Examination—an examination solution consisting of polymerase and four labeled nucleotides (dATP, dCTP, dGTP and dTTP) is introduced to the flow cell under conditions to form stabilized ternary complexes consisting of each primer-template hybrid with a polymerase and a next correct nucleotide. The ternary complexes are detected under conditions to distinguish signals produced by each of the nucleotides when participating in ternary complexes.

(2) Deblocking—the examination solution is removed from the flow cell and replaced with a deblocking reagent that removes the reversible terminator moieties from the primers, thereby rendering the primers extendable.

(3) Single nucleotide extension—the deblocking solution is removed from the flow cell and four reversibly terminated nucleotides ($_{rt}$dTTP, $_{rt}$dATP, $_{rt}$dCTP and $_{rt}$dGTP) are introduced to the flow cell. The reversibly terminated nucleotides are not labeled. The flow cell is incubated in conditions that allow the next correct nucleotide to be added to the primer.

(4) Repeat steps (1) through (3) 99 times to obtain a 100 base read that covers a first end region of the template and to produce a primer extension product that is hybridized to the first region.

(B) Determination of a signature dinucleotide series for a second region of the template—Steps (1) through (5) of Example 1 are carried out using the primer extension product that is hybridized to the first region of the template. The steps are repeated a desired number of times or until signal to noise decays to a point that indicates the run is complete.

The result of the above sequencing procedure is a collection of reads that include two regions: a single-nucleotide resolution region and dinucleotide series signature region. The reads can be aligned to a reference genome based on the juxtaposition of the two regions. The dinucleotide signature region of each read, although lower resolution can help confirm the alignment of the single-nucleotide resolution region of the read. The dinucleotide signature region of each read can also assist with phasing of reads, for example, when single nucleotide polymorphisms (SNPs) are distinguished in the signature and when the length of the reads is long enough to cover SNPs that form a haplotype.

Example 4

Paired Read Sequencing Using Single Nucleotide Resolution Methods Coupled with Dinucleotide Signature Determination This example describes a method for identifying a template sequence by determining the sequences for two regions of the template at single nucleotide resolution and determining a signature dinucleotide series for an intervening region of the template. The resulting read can be aligned using known paired read methods (also known in the art as "paired end" methods) with the added benefit of using the signature region to confirm the alignment.

A plurality of template nucleic acids are attached to the inner surface of an optically transparent flow cell. Primers are hybridized to the template nucleic acids. The primers include a 3' reversible terminator moiety (e.g. the terminator moiety having been introduced via chemical synthesis or via polymerase catalyzed extension using a reversibly terminated nucleotide).

The primed nucleic acid templates are subjected to a Sequencing By Binding™ procedure as follows:

(A) Single nucleotide resolution SBB™ procedure for a first region of a template—examination, deblocking, and single nucleotide extension are carried out as set forth in step (A) of Example 3. The procedure determines a 100 base read that covers a first end region of the template and produces a primer extension product that is hybridized to the first region.

(B) Determination of a signature dinucleotide series for an intervening region of the template—Step (B) of Example 1 is carried out using the primer extension product that is hybridized to the first region of the template. The steps are repeated a desired number of times or until signal to noise decays to a pre-defined point. The result of steps (A) and (B) is a collection of reads that include two regions: a single-nucleotide resolution region (i.e. the first end region) and dinucleotide series signature region (i.e. the intervening region). The product is a primer extension product that is hybridized to the first and second regions (C) Single nucleotide resolution SBB™ procedure for a second end region of a template—Step (A) is carried out using the primer extension product that is hybridized to the first and second regions of the template.

The result of steps (A) through (C) is a collection of reads that include three regions: a first single-nucleotide resolution region (first end region) a dinucleotide series signature region (intervening region) and a second single-nucleotide resolution region (second end region). The reads can be aligned to a reference genome based on the proximity of the first and second end regions. The intervening region of each read, although lower resolution, can help confirm the alignment of the single-nucleotide resolution, end regions of the read. The dinucleotide signature region of each read can also assist with phasing of reads, for example, when the length of the reads across the combined regions is long enough to cover SNPs that form a haplotype.

Example 5

Mixed Extension Using 2 Extendible Nucleotides and 2 Reversibly Terminated Nucleotides This example describes a method for determining dinucleotide series for a template nucleic acid. The dinucleotide series, alone or in combination, can be used as a signature for the template. Two or more of the dinucleotide series can be aligned to determine the sequence of the template at single nucleotide resolution. Moreover, a third dinucleotide series can provide error checking capabilities.

A template nucleic acid is attached to the inner surface of an optically transparent flow cell. A primer is hybridized to the template nucleic acid. The primer includes a 3' reversible terminator moiety (e.g. the terminator moiety having been introduced via chemical synthesis or via polymerase catalyzed extension using a reversibly terminated nucleotide). Extension of the primer, following deblocking of the reversible terminator moiety, is expected to add the following sequence of nucleotides to the primer:

(SEQ ID NO: 4)
5'-AAATGCATTGGCAGTGTA-3'

The primed nucleic acid template is subjected to a Sequencing By Binding™ procedure as follows:

(1) 1st run examination—an examination solution consisting of polymerase and four labeled nucleotides (dATP, dCTP, dGTP and dTTP) is introduced to the flow cell under conditions to form a stabilized ternary complex consisting of the primer-template hybrid, polymerase and next correct nucleotide. The ternary complex is detected under conditions to distinguish signals produced by each of the nucleotides when participating in ternary complexes. The next correct nucleotide produces a signal indicative of dATP binding and, thus the first nucleotide for the extension product is identified as A.

(2) 1st run deblocking—the examination solution is removed from the flow cell and replaced with a deblocking reagent that removes the reversible terminator moiety from the primer, thereby rendering the primer extendable.

(3) 1st run extension—the deblocking solution is removed from the flow cell and replaced with an extension mixture that includes a polymerase, 2 extendable nucleotides (dATP and dTTP) and 2 reversibly terminated nucleotides ($_{rt}$dCTP and $_{rt}$dGTP). The nucleotides are not labeled. The flow cell is incubated in conditions that allow primer extension until the next $_{rt}$dCTP or $_{rt}$dGTP is incorporated. In one configuration, the extension and examination steps are fluidically separated by replacing the extension mixture with the examination solution. Alternatively, the extension mixture and examination solution can be present together in the flow cell (e.g. via co-delivery or additive delivery).

(4) Repeat steps (1) through (3) until signal to noise decay indicates the 1st Run is complete—the result is a series of dinucleotides [SC][SA][SG][SC][SA][ST][ST], wherein S=C or G and wherein the number and types of nucleotides between each dinucleotide is apparently ambiguous. The dinucleotide series can serve as a signature for the template. Optionally, further signature information can be obtained by carrying out the following steps on the template nucleic acid.

(5) Strip 1st run extension product—the flow cell is treated with a chemical denaturant and/or heat to remove the extended primer from the template nucleic acid.

(6) Re-apply primer—The flow cell is incubated with a primer having the same sequence and reversible terminator as was used previously, thereby re-forming the primer-template nucleic acid hybrid.

(7) 2nd run examination—the next correct nucleotide is detected as described for step (1).

(8) Deblocking is carried out as in step (2).

(9) 2nd run extension—the deblocking solution is removed from the flow cell and replaced with an extension mixture that includes a polymerase and 2 extendable nucleotides (dCTP and dGTP) and 2 reversibly terminated nucleotides ($_{rt}$dATP and $_{rt}$dTTP). The nucleotides are not labeled. The flow cell is incubated in conditions that allow primer extension until the next $_{rt}$dATP or $_{rt}$dTTP is incorporated.

(10) Repeat steps (7) through (9) until signal to noise decay indicates the 2nd Run is complete—the result is a series of dinucleotides [WA][WA][WT][WG][WT][WT][WG][WG][WG][WA], wherein W=A or T and wherein the number and types of nucleotides between each dinucleotide is apparently ambiguous.

(11) Repeat steps (5) through (10) replacing the 2nd Run extension mixture with a 3rd Run extension mixture that includes a polymerase, 2 extendable nucleotides (dTTP and dCTP) and 2 reversibly terminated nucleotides ($_{rt}$dATP and $_{rt}$dGTP). The result is a series of dinucleotides [RA][RA][RT][RC][RT][RG][RC][RG][RT][RT], wherein R=A or G and wherein the number and types of nucleotides between each dinucleotide is apparently ambiguous.

The extension mixtures used for each of the 3 runs and dinucleotide series determined from the runs are shown in Table 4.

TABLE 4

| Run | Extension Mix | Dinucleotide Series |
|---|---|---|
| 1 | A/T/$_{rt}$C/$_{rt}$G | [SC][SA][SG][SC][SA][ST][ST] wherein S = C or G |
| 2 | $_{rt}$A/$_{rt}$T/C/G | [WA][WA][WT][WG][WT][WT][WG][WG][WG][WA] wherein W = A or T |
| 3 | $_{rt}$A/T/C/$_{rt}$G | [RA][RA][RT][RC][RT][RG][RC][RG][RT][RT] wherein R = A or G |

One or more of the dinucleotide series shown in Table 4 can be used as a signature for the template. In cases where the complexity of background sequences is expected to be low, a relatively short dinucleotide series can suffice as a unique signature for the template. The longer the series the more distinguishing power it can have in backgrounds of ever increasing sequence complexity. A signature can consist of 2 or 3 of the dinucleotide series.

Moreover, the first and second dinucleotide series are orthogonal to each other and can be combined to determine the sequence of the template at single nucleotide resolution. Conceptually, the sequence can be determined by aligning the dinucleotides. The alignment can start with the first nucleotide, A, as determined from the first examination step (or as otherwise known). The second nucleotide in the sequence is understood to follow A and can thus be determined from the run in which extension terminated at $_{rt}$A (i.e. the 2nd Run). In this case the second nucleotide is A. The third nucleotide in the sequence is understood to follow A and can thus be determined from the run in which extension terminated at $_{rt}$A (i.e. the 2nd Run). The process can continue in this way, and as visually presented in the alignment of Table 5.

TABLE 5

| W A | | W T | | W G | |
|---|---|---|---|---|---|
| | W A | | W T | | S T |
| | | W T | | W G | W G |
| | | | W G | | S G | S T |

TABLE 5-continued

| S C | S C | W A |
|---|---|---|
| S A | S A |  |

A A A T G C A T T G G C A G T G T A
(SEQ ID NO: 4)

The third dinucleotide series can serve as an error check. As shown in Table 6, the dinucleotides from the 3$^{rd}$ run were correctly aligned with the sequence determined from Table 5. Specifically, all A and G bases in the sequence were aligned to an RN dinucleotide (N being any of the four nucleotides) and all RN dinucleotides were aligned to the sequence. Thus, information from the 3$^{rd}$ run indicated that the sequence identified from the 1$^{st}$ and 2$^{nd}$ runs was correct.

TABLE 6

| A A A T G C A T T G G C A G T G T A |
|---|
| (SEQ ID NO: 4) |

| R A | R C | R C | R T |
|---|---|---|---|
| R A | R T | R G |  |
| R T | R G | R T |  |

As set forth above, a sequence that is determined from two sequencing runs, using two different extension mixes having orthogonal complements of two reversibly terminated nucleotides and two extendable nucleotides, can be error checked using results of a run performed with a third different extension mix. The third run will identify errors pertaining to three types of nucleotides. One could discard a sequence read where an error has been identified (e.g. mismatch between the first and third read). If desired, a fourth run can be performed using an extension mix that is orthogonal to the third extension mix (i.e. A/$_{rt}$T/$_{rt}$C/G). The combination of all four runs would allow all random errors to be detected. Furthermore, across all four runs each nucleotide will be reversibly terminated in two different extension mixtures, which provides sufficient information to correct errors involving all four nucleotide types.

The error detection strategy described above (three reads with orthogonal combination of two natural and two blocked nucleotides) allows detection of certain (but not all) classes of errors. Additionally, the mixture of nucleotides that are present in the examination step (as described in commonly owned U.S. patent application Ser. No. 15/712,632 and U.S. Pat. No. 9,951,385 which issued therefrom, each of which is incorporated herein by reference) may detect different classes of errors thus complementing the former strategy and further improving the accuracy of sequencing by filtering out erroneous reads.

Example 6

Mixed Extension on Octet Instrument

This example demonstrates feasibility of distinguishing products of SBB™ procedures that employ a mixture of three extendable nucleotides and one reversibly terminated nucleotide during extension as compared to methods that employ four reversibly terminated nucleotides during extension, or four extendible nucleotides during extension.

A FORTEBIO® (Menlo Park, CA) Octet instrument employing biolayer interferometry to measure binding reactions at the surface of a fiber optic tip was used in a multi-well plate format. Primer-template nucleic acid hybrids biotinylated at the 5'-ends of the template strand were immobilized onto fiber optic tips functionalized with streptavidin (SA) using standard procedures. The primer included a fluorescent label on the 5' end. The Tough-22 primer-template nucleic acid hybrid in this procedure had the sequence shown in FIG. 1 as the template sequence to be read downstream of the primer. The template sequence to be read for the Tough-29 primer-template nucleic acid hybrid is shown in FIG. 2.

The cycling procedure involved the following steps:
a) Equilibration for 5 s in the solution containing all ingredients necessary for the incorporation of reversible terminators (step b) minus reversible terminator nucleotides, magnesium chloride, and DNA polymerase.
b) Extension of the hybridized primer with reversible terminators for 30 s under the conditions as describes in Hutter et al. Nucleosides, Nucleotides and Nucleic Acids 29: 879-895 (2010) (DOI: 10.1080/15257770.2010.536191), which is incorporated herein by reference.
c) Equilibration for 5 s in the solution as in the step a)
d) Cleavage for 5 s of the capping moiety on the reversible terminators under the conditions described in Hutter et al. supra.

Steps a) through d) are repeated 10 times, after which the extended primer is eluted from the fiber optic tip in dimethylformamide and analyzed by ABI 3500 capillary electrophoresis instrument.

Figure 2:
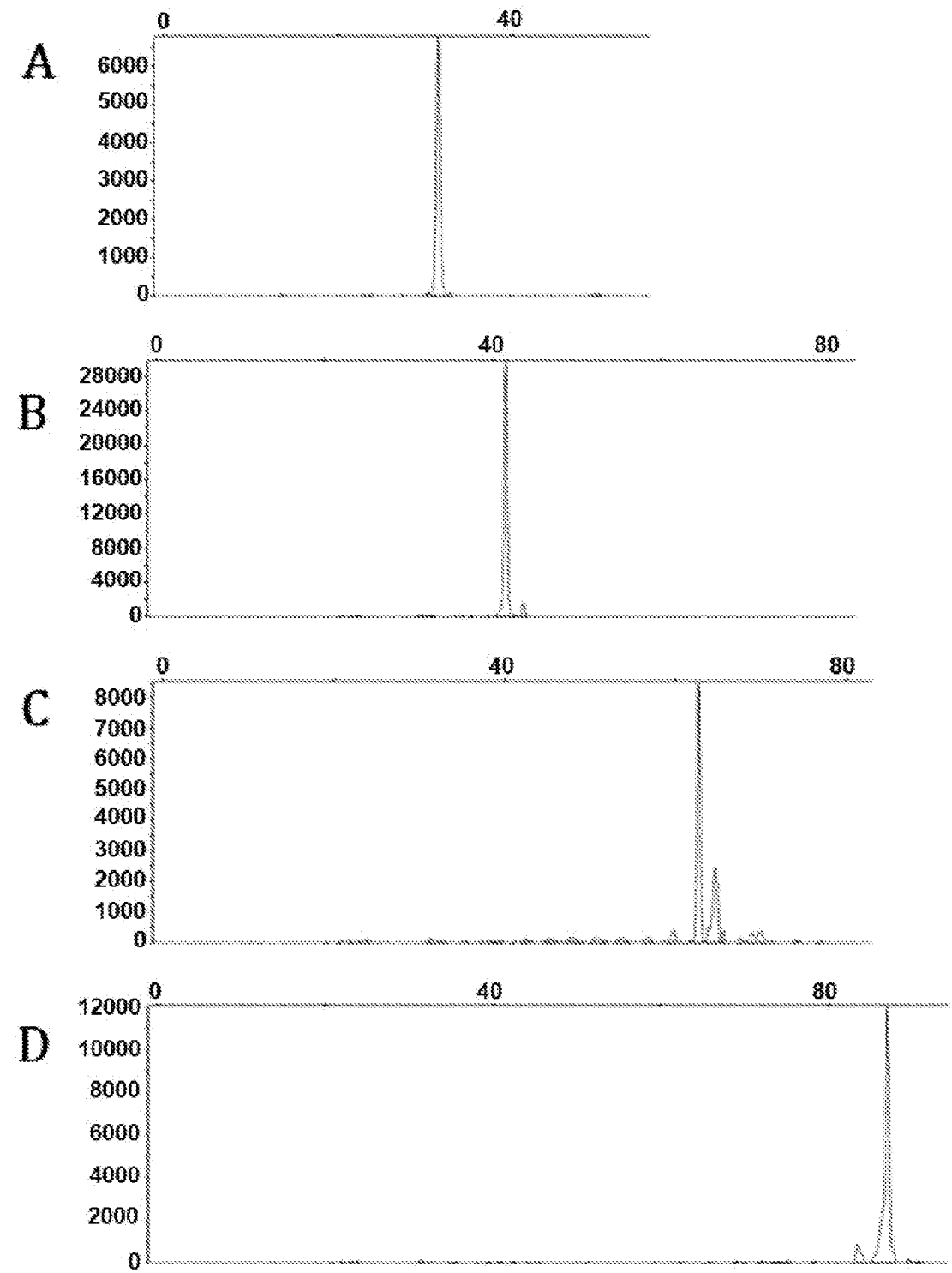
FIG. 2 shows capillary electrophoresis traces for a non-extended primer from the Tough-29 (SEQ ID NO:2) primer-template hybrid (FIG. 2A); for the primer after 10 SBB™ cycles that employ 4 reversible terminator nucleotides during the extension step (FIG. 2B); for the primer after 10 SBB™ cycles that employ a dT-aminooxy, reversible terminator nucleotide and 3 natural nucleotides during the extension step (FIG. 2C); and for the primer after 10 SBB™ cycles that employ 4 natural nucleotides during the extension step (FIG. 2D).

The results for carrying out 10 cycles of the above procedure on the Tough-22 primer-template hybrid are shown in FIG. 1. The capillary electrophoresis (CE) trace for the primer is shown in FIG. 1A. Ten extension steps each employing four reversibly terminated nucleotides were expected to extend the primer by 10 nucleotides. As shown by the CE trace in FIG. 1B, the extension was observed to be roughly equivalent to 9.6 nucleotides. Ten extension steps each employing dATP, dCTP, dGTP $_{rt}$dTTP were expected to extend the primer by 42 nucleotides. As shown by the CE trace in FIG. 1C, the extension was observed to be roughly equivalent to 39.7 nucleotides. Ten extension steps each employing four extendable terminated nucleotides were expected to extend the primer to its full length, 58 nucleotides. As shown by the CE trace in FIG. 1D, the extension was observed to be roughly equivalent to 53.1 nucleotides.

The results for carrying out 10 cycles of the above procedure on the Tough-29 primer-template hybrid are shown in FIG. 2. The capillary electrophoresis (CE) trace for the primer is shown in FIG. 2A. Ten extension steps each employing four reversibly terminated nucleotides were expected to extend the primer by 10 nucleotides. As shown by the CE trace in FIG. 2B, the extension was observed to be roughly equivalent to 10.0 nucleotides. Ten extension steps each employing dATP, dCTP, dGTP $_{rt}$dTTP were expected to extend the primer by 31 nucleotides. As shown by the CE trace in FIG. 2C, the extension was observed to be roughly equivalent to 31.2 nucleotides. Ten extension steps each employing four extendable terminated nucleotides were expected to extend the primer to its full length, 58 nucleotides. As shown by the CE trace in FIG. 2D, the extension was observed to be roughly equivalent to 55.5 nucleotides.

The measured primer extension lengths were judged to be within reasonable error of the expected lengths. Accordingly, the results demonstrate that mixtures of one reversibly terminated nucleotide and three extendable nucleotides can be used in an SBB™ procedure to increase primer extension lengths compared to the use of only reversibly terminated nucleotides.

Example 7

Re-Phasing of Nucleic Acid Sequences

Inefficiencies in primer extension and cleavage of reversible terminator moieties have cumulative effects in a sequencing protocol. Over multiple cycles, the primer molecules that fail to extend at least once during the run accumulate and cause negative phasing within a cluster or other ensemble of nucleic acids being sequenced. Negative phasing causes the dilution of the correct signal and the rise of the incorrect signal. The following sequencing protocol can be used to alleviate this problem by restoring the phased signal and coalescing it with the signal in phase:

1. Carry out single-nucleotide resolution sequencing for 100 cycles or until the signal dephases.
2. Carry out the following steps to rephase the signal:
   a. A single cycle of extension with a mixture of extendible first, second, and third nucleotide analogs and a fourth nucleotide analog that is reversibly terminated.
   b. A single cycle of extension with a mixture that includes extendable analogs of the first, second, and fourth natural nucleotides and a reversibly terminated analog of the third nucleotide.
   c. A single cycle of extension with a mixture of extendable analogs of the first, third, and fourth natural nucleotides and a reversibly terminated analog of the second nucleotide.
   d. A single cycle of extension with a mixture of extendable analogs of the second, third, and fourth natural nucleotides and a reversibly terminated analog of the first nucleotide.
3. Upon dephasing, carry out single-nucleotide resolution sequencing for another 100 cycles or until the signal dephases.
4. Repeat steps 2 and 3 until the signal and signal to noise ratio drop to the level at which bases cannot be identified with reasonably certainty.

Step 2 of this strategy allows for the negatively phased sequence to "catch" up and synchronize with the main "full-length" sequence. The effect of the rephasing step 2 is illustrated in Table 7 below using the following model sequence:

(SEQ ID NO: 5)
TGCCATCTCGAAAAACATTTGGACTGCTCCGCTTCCTCCTGAGACTGAGCT

First, second, third, and fourth nucleotides correspond to dA, dC, dG, and dT, respectively.

TABLE 7

|  | N, in phase primer | N-1, negatively phased primer |
|---|---|---|
| After n cycles | TGC | TG |
| After cycle 2a | TGCCAT | TGCCAT |
| After cycle 2b | TGCCATCTCG (SEQ ID NO: 6) | TGCCATCTCG (SEQ ID NO: 6) |
| After cycle 2c | TGCCATCTCGAAAAAC (SEQ ID NO: 7) | TGCCATCTCGAAAAAC (SEQ ID NO: 7) |
| After cycle 2d | TGCCATCTCGAAAAACA (SEQ ID NO: 8) | TGCCATCTCGAAAAACA (SEQ ID NO: 8) |

Example 8

Paired Read Sequencing Using Single Nucleotide Resolution Methods Coupled with Dark Extension This example describes a method for identifying a template sequence by determining the sequences for first and second regions of the template at single nucleotide resolution and determining the length for a linker region of the template via counting extension steps. In this example, the linker region intervenes the first and second regions such that the sequence reads for the first and second regions provide paired reads. In this exemplary method, a primer is extended through the first region using cycles that include detection steps, the extended primer is then further extended through the linker region using cycles that do not include detection steps, and the further extended primer is then extended through the second region using cycles that include detection steps.

A plurality of template nucleic acids is attached to the inner surface of an optically transparent flow cell. Primers are hybridized to the template nucleic acids. The primers include a 3' reversible terminator moiety.

The primed nucleic acid templates are subjected to a Sequencing By Binding™ procedure as follows:
  (A) Single nucleotide resolution SBB™ procedure for a first region of a template—examination, deblocking, and single nucleotide extension are carried out as set forth in step (A) of Example 3. The procedure determines a 100 base read that covers a first end region of the template and produces a primer extension product that is hybridized to the first region.
  (B) Determination of a signature nucleotide count for an intervening region of the template—the primer extension product that is hybridized to the first region of the template following step (A) is subjected to cycles of a modified SBB™ procedure. The modification is to omit the examination steps used in step (A) such that each cycle includes deblocking and single nucleotide extension using blocked nucleotides. The cycles are repeated a desired number of times. The result of steps (A) and (B) is a collection of reads that include two regions: a single-nucleotide resolution region (i.e. the first region) and a length, counted in number of nucleotide positions for a linker region that is immediately adjacent to the first region. The product is a primer extension product that is hybridized to the first region and linker regions (C) Single nucleotide resolution SBB™ procedure for a second region of a template—The procedure in step (A) is carried out using the primer extension product that is hybridized to the first and second regions of the template after completing step (B).

The result of steps (A) through (C) is a collection of reads that include three regions: a first single-nucleotide resolution region, a signature nucleotide count for a linker region, and a second single-nucleotide resolution region. The reads can be aligned to a reference genome based on the proximity of the first and second end regions. The length of the linker region can inform alignment of the first and second single-nucleotide resolution regions by constraining the distance between the reads when aligned to a reference genome. The signature region of each read can also assist with phasing of reads, for example, when the length of the reads across the combined regions is long enough to cover SNPs that form a haplotype. Exemplary algorithms for assembling paired reads to determine genomic sequences include, but are not limited to, those set forth in Hormozdiari et al., Combinatorial Algorithms for Structural Variation Detection in High-Throughput Sequenced Genomes. *Genome Research* 19:1270-1278 (2009) or Sindi et al., A geometric approach for classification and comparison of structural variants. *Bioinformatics* 25: i222-i230 (2009), each of which is incorporated herein by reference, or others known in the art.

An advantage of the paired read technique set forth in this example is to avoid detection steps that have adverse consequences for sequencing accuracy and read length. Although not intending to be limited by mechanism, excitation of fluorophores during fluorescence detection steps used in the single nucleotide resolution SBB™ procedure is believed to cause photodamage to the nucleic acid being sequenced and to reagents used for sequencing. Because sequencing is a cumulative process, this photodamage not only impacts accuracy of individual base calls in a sequence read but it also results in shortened read length due to cumulative effects of signal decay and/or accumulation of errors over the run.

Although short reads from multiple genomic fragments can be assembled to reconstruct a larger chromosome from which the fragments were derived, certain types of structural information cannot be unambiguously inferred from the assembled sequence. Taking the example of a diploid organism, such as a human, it can be difficult to determine whether polymorphisms observed in reads from two separate fragments are derived from the same parent or different parents. However, if the two reads are linked via paired reads as set forth in this example, it can be determined that the reads are from the same strand and thus from the same parent. Accordingly, paired read methods set forth herein provide an advantage of identifying structural features of a genome (e.g. haplotypes) that are not easily obtained from single read methods.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. A method of characterizing a nucleic acid, comprising
   (a) extending a primer-template nucleic acid hybrid comprising a primer and a template nucleic acid with extendable nucleotide cognates and a nucleotide cognate comprising a reversible terminator moiety to produce an extended primer-template hybrid comprising the reversible terminator moiety;
   (b) forming a stabilized ternary complex comprising the extended primer-template hybrid, a polymerase and a nucleotide cognate of the next base in the template nucleic acid;
   (c) detecting the stabilized ternary complex to distinguish the next base;
   (d) deblocking the extended primer-template hybrid;
   (e) repeating steps (a) through (d) using the extended primer-template hybrid as the primer-template nucleic acid hybrid to determine a series of base multiplets in the template nucleic acid;
   (f) repeating steps (a) through (e) to determine at least 3 different series of base multiplets in the template nucleic acid each time; and
   (g) combining at least four different series of base multiplets to determine a sequence of the nucleic acid.

2. The method of claim 1, wherein step (f) comprises repeating steps (a) through (e) exactly three times, wherein a different nucleotide is reversibly terminated each time.

3. The method of claim 1, wherein step (f) comprises removing the extended primer and hybridizing a new primer to the template nucleic acid, thereby forming a new primer-template nucleic acid hybrid before repeating steps (a) through (e).

4. The method of claim 1, wherein at least one series of base multiplets is determined when 2 nucleotide cognates each comprise a reversible terminator moiety in step (a).

5. The method of claim 1, wherein the nucleotide cognate comprising the reverse terminator moiety of step (a) does not comprise an exogenous label.

6. The method of claim 1, wherein extending of step (a) further comprises a polymerase in a mixture comprising at least one of the nucleotide cognates.

7. The method of claim 1, wherein the extended primer-template hybrid of step (a) is the product of polymerase extension during a sequencing process, wherein the sequencing process detects signals indicative of a sequence of the template nucleic acid that is 3' to the series of at least two base multiplets.

8. The method of claim 7, further comprising a computer assisted process of aligning the sequence of the template nucleic acid to a region of a reference genome, wherein the aligning is performed by aligning the region of the reference genome to the sequence of the template nucleic that is 3' to the series of at least two base multiplets.

9. The method of claim 8, further comprising performing polymerase extension of the extended primer in a second sequencing process, wherein the second sequencing process detects signals indicative of a sequence of the template nucleic acid that is 5' to the series of at least two base multiplets.

10. The method of claim 9, further comprising the computer assisted process of aligning the sequence of the template to a region of the reference genome, wherein the aligning is performed by aligning the region of the reference genome to the sequence of the template nucleic acid that is 3' to the series of at least two base multiplets, the series of at least two base multiplets, and the sequence of the template that is 5' to the series to at least two base multiplets.

11. The method of claim 1, wherein at least one of the nucleotide cognates comprises an exogenous label that is detected in step (c).

12. The method of claim 1, wherein the nucleotide cognates each do not comprise an exogenous label that is detected in step (c).

13. The method of claim 1, wherein the polymerase comprises an exogenous label that is detected in step (c).

14. The method of claim 1, wherein the extendable nucleotide cognates of step (a) are in a mixture.

15. A method of characterizing a template nucleic acid, wherein the template comprises a linker region that is adjacent to and between first and second regions of the template nucleic acid, comprising steps of
   (a) obtaining a single base resolution sequence of the first region by extending a primer along the first region of the template nucleic acid, thereby producing an extended primer-template hybrid;
   (b) obtaining a signature for the linker region by
      (i) further extending the extended primer of the extended primer-template hybrid using a mixture of nucleotides, wherein the mixture of nucleotides comprises nucleotide cognates of first, second, third and fourth different base types, wherein the nucleotide cognate of the first base type comprises a reversible terminator, and wherein at least one of the nucleotide cognates of the second, third or fourth base types is extendable, and
      (ii) detecting a stabilized ternary complex, the stabilized ternary complex comprising the further extended primer-template hybrid, a polymerase and a nucleotide cognate of the next base in the template, wherein the signature comprises a base multiplet comprising the first base type followed by the next base; and
   (c) obtaining a single base resolution sequence of the second region by extending the further extended primer of the further extended primer-template hybrid.

16. A method of characterizing a nucleic acid, comprising:
   (a) extending a primer-template nucleic acid hybrid with a polymerase and a mixture of nucleotide cognates of first, second, third and fourth different base types to produce an extended primer hybrid, wherein the nucleotide cognate of the first base type comprises a reversible terminator, wherein at least one of the nucleotide cognates of the second, third or fourth base types is extendable;
   (b) contacting the extended primer hybrid with at least one nucleotide cognate to form a stabilized ternary complex comprising a nucleotide cognate of the next base in the template;
   (c) detecting the stabilized ternary complex to distinguish the next base, thereby determining the presence of a base multiplet in the template nucleic acid comprising the first base type followed by the next base.

17. The method of claim 16, further comprising:
   (d) deblocking the extended primer hybrid comprising the nucleotide cognate for the first base type comprising the reversible terminator and repeating steps (a) through (c) using the extended primer hybrid as the primer-template nucleic acid hybrid, thereby determining a series of at least two base multiplets in the template nucleic acid.

18. The method of claim 17, further comprising:
   (e) repeating steps (a) through (d), wherein the nucleotide cognate of the second base type comprises a reversible terminator, and wherein nucleotide cognates of the first, third and fourth base types are extendable, and wherein the base multiplet determined in step (c) comprises the second base type followed by the next base, thereby determining two series of base multiplets in the template nucleic acid.

19. The method of claim 18, further comprising:
(e) repeating steps (a) through (d), wherein the nucleotide cognate of the third base type comprises a reversible terminator, and wherein nucleotide cognates of the first, second and fourth base types are extendable, and wherein the base multiplet determined in step (c) comprises the third base type followed by the next base; and
(f) repeating steps (a) through (d), wherein the nucleotide cognate of the fourth base type comprises a reversible terminator, and wherein nucleotide cognates of the first, second and third base types are extendable, and wherein the base multiplet determined in step (c) comprises the fourth base type followed by the next base;
thereby determining four series of base multiplets in the template nucleic acid.

\* \* \* \* \*

SEQUENCE LISTING

<160> NUMBER OF SEQ ID NOS: 8

<210> SEQ ID NO 1
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 1
tgagtcaaaa aaaaaaaaa aaaaggctac tcctttctc ctgcttccaa ttttctga        58

<210> SEQ ID NO 2
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 2
cgaatgtgct gctgctgctg ctgctgctgc tgctgcggtc tcctgggaaa ggctctca        58

<210> SEQ ID NO 3
<211> LENGTH: 25
<212> TYPE: DNA
<213> ORGANISM: Artificial Sequence
<220> FEATURE:

```
<223> OTHER INFORMATION: Synthetic polynucleotide

<400> SEQUENCE: 3
tagccatctg actaacctac tgttt                                         25

<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 4
aaatgcattg gcagtgta                                                 18

<210> SEQ ID NO 5
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 5
tgccatctcg aaaaacattt ggactgctcc gcttcctcct gagactgagc t            51

<210> SEQ ID NO 6
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 6
tgccatctcg                                                          10

<210> SEQ ID NO 7
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 7
tgccatctcg aaaaac                                                   16

<210> SEQ ID NO 8
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 8
tgccatctcg aaaaaca                                                  17
```